(12) United States Patent
De Buyl et al.

(10) Patent No.: US 7,638,613 B2
(45) Date of Patent: Dec. 29, 2009

(54) XYLANASE, MICROORGANISMS PRODUCING IT, DNA MOLECULES, METHODS FOR PREPARING THIS XYLANASE AND USES OF THE LATTER

(75) Inventors: Eric De Buyl, Linkebeek (BE); Andrée Lahaye, Brussels (BE); Pierre Ledoux, Brussels (BE); René Detroz, Lasne (BE)

(73) Assignee: Genencor International, Inc., Palo Alto, CA (US)

( * ) Notice: Subject to any disclaimer, the term of this patent is extended or adjusted under 35 U.S.C. 154(b) by 260 days.

(21) Appl. No.: 11/178,031

(22) Filed: Jul. 8, 2005

(65) Prior Publication Data

US 2006/0020122 A1  Jan. 26, 2006

Related U.S. Application Data

(62) Division of application No. 09/909,207, filed on Jul. 19, 2001, now Pat. No. 7,022,827.

(51) Int. Cl.
  C07H 21/04      (2006.01)
  C12N 15/00     (2006.01)
  C12N 15/75     (2006.01)

(52) U.S. Cl. .................. 536/23.1; 435/320.1; 435/222; 435/485

(58) Field of Classification Search ................ 536/23.1; 435/320.1, 485, 222
  See application file for complete search history.

(56) References Cited

U.S. PATENT DOCUMENTS

| 4,462,884 A | 7/1984 | Carles et al. .................. 162/56 |
| 5,306,633 A | 4/1994 | Gottschalk .................. 435/200 |
| 5,352,603 A | 10/1994 | Vetter et al. .................. 435/221 |
| 5,770,424 A | 6/1998 | Outtrup et al. .............. 435/200 |
| 6,140,095 A | 10/2000 | Williams et al. ............ 435/200 |

FOREIGN PATENT DOCUMENTS

| EP | 0 507 723 | 3/1992 |
| EP | 0 634 490 | 11/1994 |
| WO | WO 94/04664 | 3/1994 |
| WO | WO 94/01532 | 10/1994 |
| WO | WO 95/18219 | 7/1995 |

OTHER PUBLICATIONS

Akjba et al. 1988 *Methods in Enzy,p;pgu* 160:655-659.
Bailey et al., "Interlaboratory Testing of Methods for Assay of Xylanase Activity," *Journal of Biotechnology*, 1992, V. 23:257-270.
Dey et al. 1992 *Can. J. Microbiology* 38 (5) p. 436-442.
Fukusaki et al., "The complete Nucleotide Sequence of the Xylanase Gene (xynA) of *Bacillus pumilus*," *FEBS letters*, V. 171(2), pp. 197-201.
Gupta et al., "A Thermostable Extracellar Xylanase from Alkalophilic *Bacillus* sp. NG-27," *Biotechnology Letters*, V. 14(11):1045-1046 (1992).
Irwin et al., "Characterization and Sequence of *Thermomonospora fusca* Xylanase", *Applied and Environmental Microbiology*, 60(3):763-770 Mar. 1994.
Khasin et al. 1993 *Applied and Environmental Microbiology* 59 (6) 1725-30.
Nakamura et al., "Thermophilic Alkaline Xylanase from Newly Isolated Alkalophilic and Thermophilic *Bacillus* sp. strain TAR-1", *Bioscience, Biotechnology, and Biochemistry*, 58(1):78-81 Jan. 1994.
Okazaki et al., "Purification and Characterization of Xylanases from Alkalophilic Themophilic *Bacillus* spp;,", *Agricultural and Biological Chemistry*, 49(7):2033-2039 (1985).
Yu Ju Jyun et al., "Nucleotide Sequence and Analysis of a Xylanase Gene (xynS) from Alkali-Tolerant *Bacillus* sp. YA-14 and Comparison with other Xylanases," Journal of Microbiology and Biotechnology, V. 3(3) pp. 139-145 (1993).

*Primary Examiner*—Gary Benzion
*Assistant Examiner*—Cynthia B Wilder

(57) ABSTRACT

The invention relates to a xylanase originating from a *Bacillus* strain. This xylanase is active over a wide range of acid and basic pH.

The invention also relates to new strains of microorganisms producing this xylanase and to methods for preparing this xylanase.

The invention also relates to a DNA molecule and to an expression vector or an integration vector containing this DNA molecule.

The invention also relates to uses of the latter and to compositions containing it.

5 Claims, 13 Drawing Sheets

| | | | | | | | | | | | | | | |
|---|---|---|---|---|---|---|---|---|---|---|---|---|---|---|
| CAA | ATC | GTC | ACC | GAC | AAT | TCC | ATT | GGC | AAC | CAC | GAT | GGC | TAT | GAT | TAT |
| Gln | Ile | Val | Thr | Asp | Asn | Ser | Ile | Gly | Asn | His | Asp | Gly | Tyr | Asp | Tyr |
| 1 | | | | 5 | | | | | 10 | | | | | 15 | |

```
CAA ATC GTC ACC GAC AAT TCC ATT GGC AAC CAC GAT GGC TAT GAT TAT
Gln Ile Val Thr Asp Asn Ser Ile Gly Asn His Asp Gly Tyr Asp Tyr
 1           5                   10                  15

GAA TTT TGG AAA GAT AGC GGT GGC TCT GGG ACA ATG ATT CTC AAT CAT
Glu Phe Trp Lys Asp Ser Gly Gly Ser Gly Thr Met Ile Leu Asn His
             20                  25                  30

GGC GGT ACG TTC AGT GCC CAA TGG AAC AAT GTT AAC AAC ATA TTA TTC
Gly Gly Thr Phe Ser Ala Gln Trp Asn Asn Val Asn Asn Ile Leu Phe
             35                  40                  45

CGT AAA GGT AAA AAA TTC AAT GAA ACA CAA ACA CAC CAA CAA GTT GGT
Arg Lys Gly Lys Lys Phe Asn Glu Thr Gln Thr His Gln Gln Val Gly
         50                  55                  60

AAC ATG TCC ATA AAC TAC GGA GCC AAC TTC CAA CCA AAT GGT AAT GCG
Asn Met Ser Ile Asn Tyr Gly Ala Asn Phe Gln Pro Asn Gly Asn Ala
 65              70                  75                      80

TAT TTA TGC GTC TAT GGT TGG ACT GTT GAC CCT CTT GTC GAA TAT TAT
Tyr Leu Cys Val Tyr Gly Trp Thr Val Asp Pro Leu Val Glu Tyr Tyr
                 85                  90                  95

ATT GTC GAC AGT TGG GGC AAC TGG CGT CCA CCA GGA GCA ACG CCT AAG
Ile Val Asp Ser Trp Gly Asn Trp Arg Pro Pro Gly Ala Thr Pro Lys
                 100                 105                 110

GGG ACC ATC ACT GTT GAT GGA GGA ACA TAT GAT ATC TAC GAG ACT CTT
Gly Thr Ile Thr Val Asp Gly Gly Thr Tyr Asp Ile Tyr Glu Thr Leu
             115                 120                 125

AGA GTC AAT CAA CCC TCC ATT AAG GGG ATT GCC ACA TTT AAA CAA TAT
Arg Val Asn Gln Pro Ser Ile Lys Gly Ile Ala Thr Phe Lys Gln Tyr
             130                 135                 140

TGG AGT GTT CGA AGA TCG AAA CGC ACG AGT GGC ACG ATT TCT GTC AGC
Trp Ser Val Arg Arg Ser Lys Arg Thr Ser Gly Thr Ile Ser Val Ser
145                 150                 155                 160
```

FIG._1A

```
AAC CAC TTT AGA GCG TGG GAA AAC TTA GGG ATG AAT ATG GGG AAA ATG
Asn His Phe Arg Ala Trp Glu Asn Leu Gly Met Asn Met Gly Lys Met
            165             170             175

TAT GAA GTC GCG CTT ACT GTA GAA GGC TAT CAA AGT AGC GGA AGT GCT
Tyr Glu Val Ala Leu Thr Val Glu Gly Tyr Gln Ser Ser Gly Ser Ala
            180             185             190

AAT GTA TAT AGC AAT ACA CTA AGA ATT AAC GGT AAC CCT CTC TCA ACT
Asn Val Tyr Ser Asn Thr Leu Arg Ile Asn Gly Asn Pro Leu Ser Thr
            195             200             205

ATT AGT AAT GAC GAG AGC ATA ACT TTG GAT AAA AAC AAT
Ile Ser Asn Asp Glu Ser Ile Thr Leu Asp Lys Asn Asn
            210             215             220
```

FIG._1B

```
AAATTGAATT GTGTATATCT AATGATAACG ACAAATCGTC ACTGTTTTTA AACTAATCTC

AAACCAATAC TTCTTTATTT AACGCTAACC ACTTGCAATC TTATCACAAG AACATTCTTT

ATAGGAACTT TCCCATTTGC AAGACGATAA AAAATCTTTT TCCCCTATTT TATCTTATCG

CCTTGATCGG TTTAATTTGT AAACTTTATT TTAGTTTACG TGATGTTCCC TCATTCATAC

CATTAATCAC AGTTAACGCT AGAGTCATCT TTTTTCGGTT CTCAAAAATA CCTGAAGAAC

ATTTATGTCA TATTTTCTCA CGCCGCTCCA TAATGGAATA TATATACTCT TTTATACATA

TTAAGTAAAT TAGTATATAC TTGCGTTATC AAAATGTGAG ATAATCTAAT TGATCAAACA

AGCAGCTATC CAAAAAACAC TGATGTTGAC CTCTTAAAGA AGTGTCACTA TCTATGAAAA

GATAATTATC CAGTTTCAAA ATTTGAAATA GTGTGTATGG AATAGTTTGA ATGTCAACTG

CTGTGAAAGG AGGGTAGGTA GTACCGTAGA CTTCATTACC AAAAATTAGT TGTAAAAAAA
```

| | | | | | | | | | | | |
|---|---|---|---|---|---|---|---|---|---|---|---|
| TTAAAAGGAG GAATGCCTA | ATG | AGA | CAA | AAG | AAA | TTG | ACG | TTG | ATT | TTA | GCC |
| | Met | Arg | Gln | Lys | Lys | Leu | Thr | Leu | Ile | Leu | Ala |
| | | −25 | | | | | | −20 | | | |

| TTT | TTA | GTT | TGT | TTT | GCA | CTA | ACC | TTA | CCT | GCA | GAA | ATA | ATT | CAG | GCA |
|---|---|---|---|---|---|---|---|---|---|---|---|---|---|---|---|
| Phe | Leu | Val | Cys | Phe | Ala | Leu | Thr | Leu | Pro | Ala | Glu | Ile | Ile | Gln | Ala |
| −15 | | | | | −10 | | | | | −5 | | | | | |

| CAA | ATC | GTC | ACC | GAC | AAT | TCC | ATT | GGC | AAC | CAC | GAT | GGC | TAT | GAT | TAT |
|---|---|---|---|---|---|---|---|---|---|---|---|---|---|---|---|
| Gln | Ile | Val | Thr | Asp | Asn | Ser | Ile | Gly | Asn | His | Asp | Gly | Tyr | Asp | Tyr |
| 1 | | | | 5 | | | | | 10 | | | | | 15 | |

| GAA | TTT | TGG | AAA | GAT | AGC | GGT | GGC | TCT | GGG | ACA | ATG | ATT | CTC | AAT | CAT |
|---|---|---|---|---|---|---|---|---|---|---|---|---|---|---|---|
| Glu | Phe | Trp | Lys | Asp | Ser | Gly | Gly | Ser | Gly | Thr | Met | Ile | Leu | Asn | His |
| | | | 20 | | | | 25 | | | | | 30 | | | |

| GGC | GGT | ACG | TTC | AGT | GCC | CAA | TGG | AAC | AAT | GTT | AAC | AAC | ATA | TTA | TTC |
|---|---|---|---|---|---|---|---|---|---|---|---|---|---|---|---|
| Gly | Gly | Thr | Phe | Ser | Ala | Gln | Trp | Asn | Asn | Val | Asn | Asn | Ile | Leu | Phe |
| | | | 35 | | | | 40 | | | | | 45 | | | |

| CGT | AAA | GGT | AAA | AAA | TTC | AAT | GAA | ACA | CAA | ACA | CAC | CAA | CAA | GTT | GGT |
|---|---|---|---|---|---|---|---|---|---|---|---|---|---|---|---|
| Arg | Lys | Gly | Lys | Lys | Phe | Asn | Glu | Thr | Gln | Thr | His | Gln | Gln | Val | Gly |
| | 50 | | | | | 55 | | | | | 60 | | | | |

| AAC | ATG | TCC | ATA | AAC | TAC | GGA | GCC | AAC | TTC | CAA | CCA | AAT | GGT | AAT | GCG |
|---|---|---|---|---|---|---|---|---|---|---|---|---|---|---|---|
| Asn | Met | Ser | Ile | Asn | Tyr | Gly | Ala | Asn | Phe | Gln | Pro | Asn | Gly | Asn | Ala |
| 65 | | | | 70 | | | | | 75 | | | | | 80 | |

FIG._2A

```
TAT TTA TGC GTC TAT GGT TGG ACT GTT GAC CCT CTT GTC GAA TAT TAT
Tyr Leu Cys Val Tyr Gly Trp Thr Val Asp Pro Leu Val Glu Tyr Tyr
            85                  90                  95

ATT GTC GAC AGT TGG GGC AAC TGG CGT CCA CCA GGA GCA ACG CCT AAG
Ile Val Asp Ser Trp Gly Asn Trp Arg Pro Pro Gly Ala Thr Pro Lys
            100                 105                 110

GGG ACC ATC ACT GTT GAT GGA GGA ACA TAT GAT ATC TAC GAG ACT CTT
Gly Thr Ile Thr Val Asp Gly Gly Thr Tyr Asp Ile Tyr Glu Thr Leu
            115                 120                 125

AGA GTC AAT CAA CCC TCC ATT AAG GGG ATT GCC ACA TTT AAA CAA TAT
Arg Val Asn Gln Pro Ser Ile Lys Gly Ile Ala Thr Phe Lys Gln Tyr
            130                 135                 140

TGG AGT GTT CGA AGA TCG AAA CGC ACG AGT GGC ACG ATT TCT GTC AGC
Trp Ser Val Arg Arg Ser Lys Arg Thr Ser Gly Thr Ile Ser Val Ser
145                 150                 155                 160

AAC CAC TTT AGA GCG TGG GAA AAC TTA GGG ATG AAT ATG GGG AAA ATG
Asn His Phe Arg Ala Trp Glu Asn Leu Gly Met Asn Met Gly Lys Met
            165                 170                 175

TAT GAA GTC GCG CTT ACT GTA GAA GGC TAT CAA AGT AGC GGA AGT GCT
Tyr Glu Val Ala Leu Thr Val Glu Gly Tyr Gln Ser Ser Gly Ser Ala
            180                 185                 190

AAT GTA TAT AGC AAT ACA CTA AGA ATT AAC GGT AAC CCT CTC TCA ACT
Asn Val Tyr Ser Asn Thr Leu Arg Ile Asn Gly Asn Pro Leu Ser Thr
            195                 200                 205

ATT AGT AAT GAC GAG AGC ATA ACT TTG GAT AAA AAC AAT TAAAAATCCT
Ile Ser Asn Asp Glu Ser Ile Thr Leu Asp Lys Asn Asn
            210                 215                 220

TATCTCTTTC GGTTCAGTTC TCATTATTTT CAAATAACCT CCCGGTTGGA TCTTTTCCAA

CGGGAGGTTT TATTGGAAAG GTTAAGTATA GTATACTCCG ATTCCATCCA GAGGAATGCT

TGAAACACCT CCGTCACTAG
```

FIG._2B

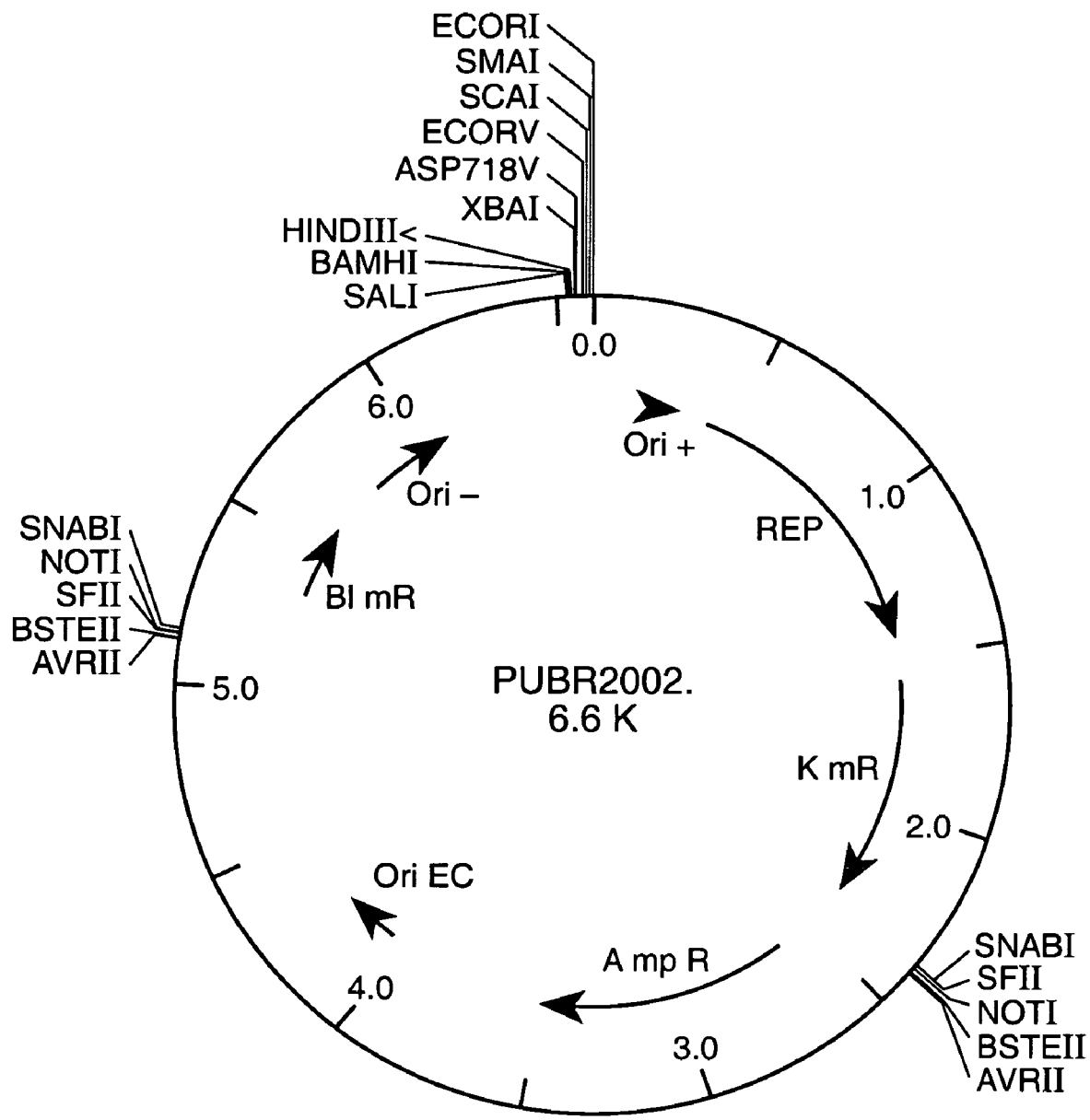
FIG._3

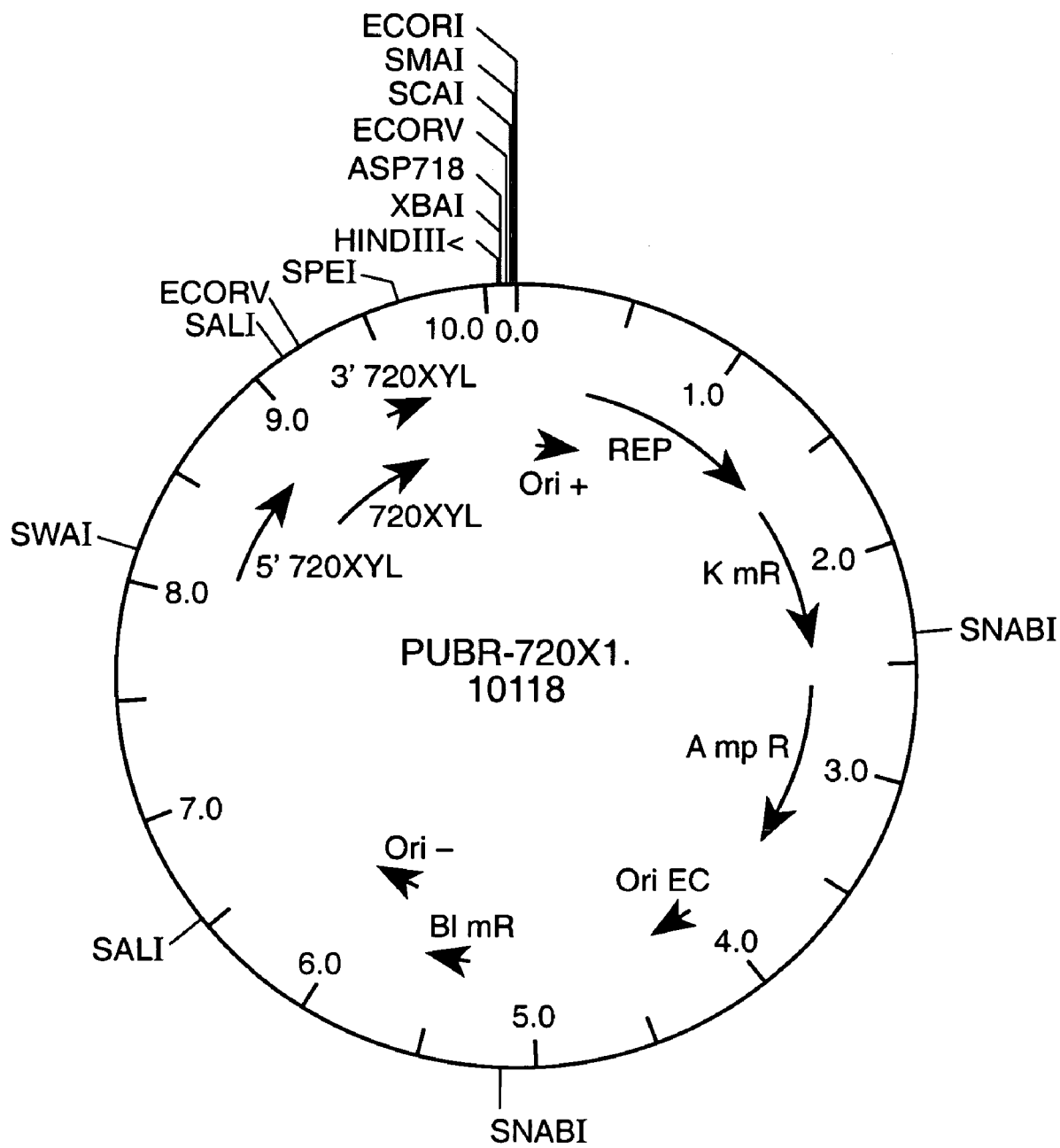
FIG._4

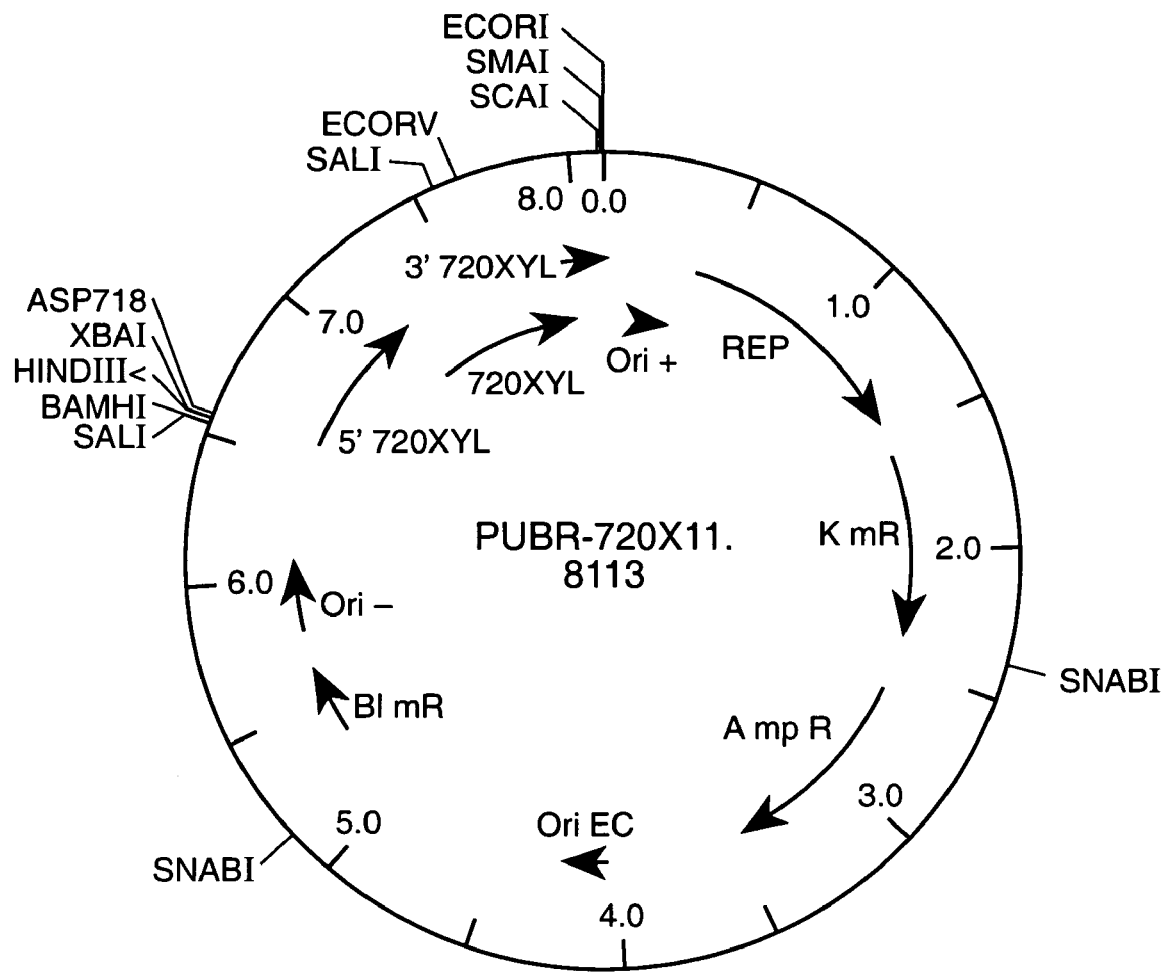
FIG._5

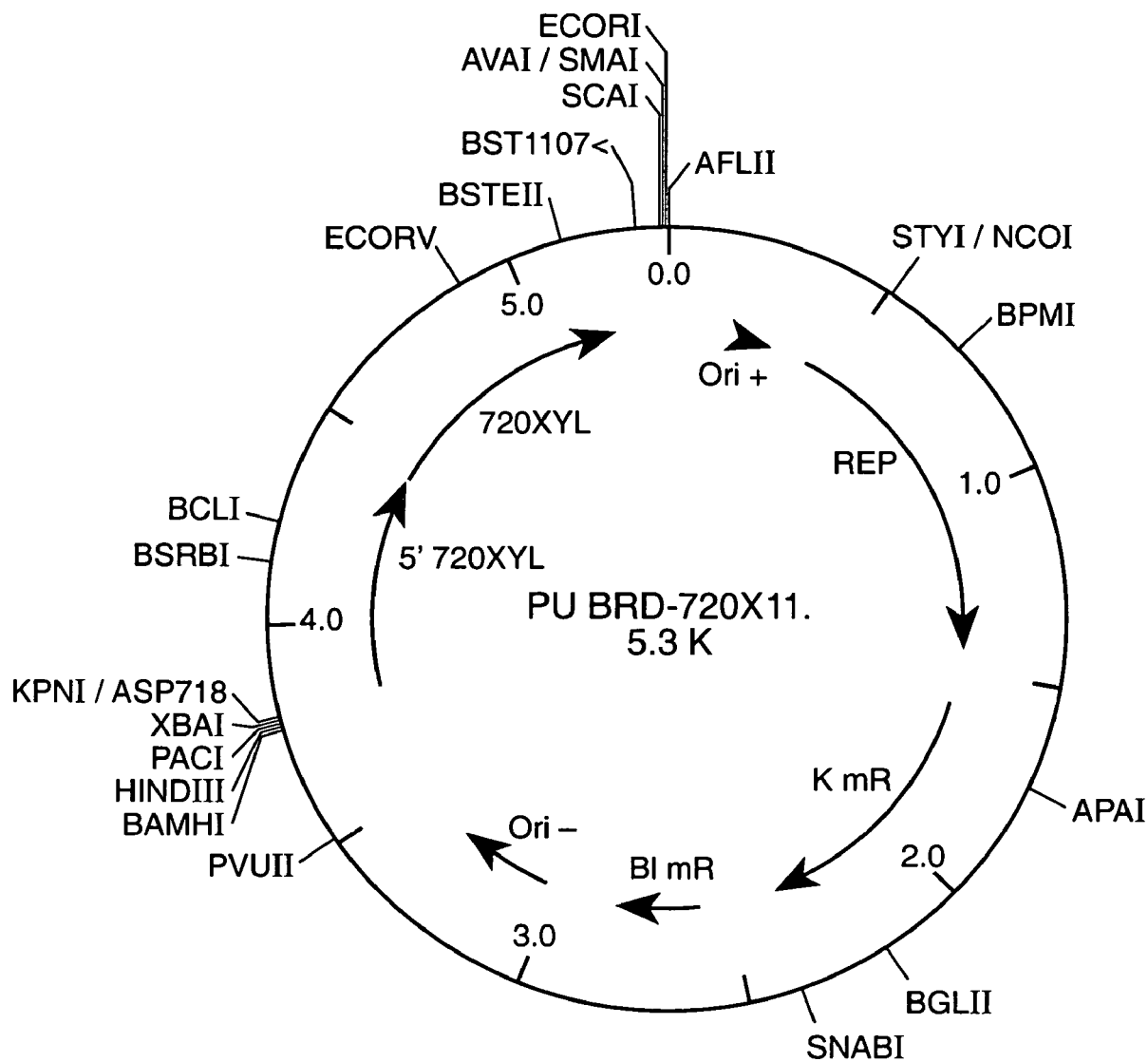
FIG._6

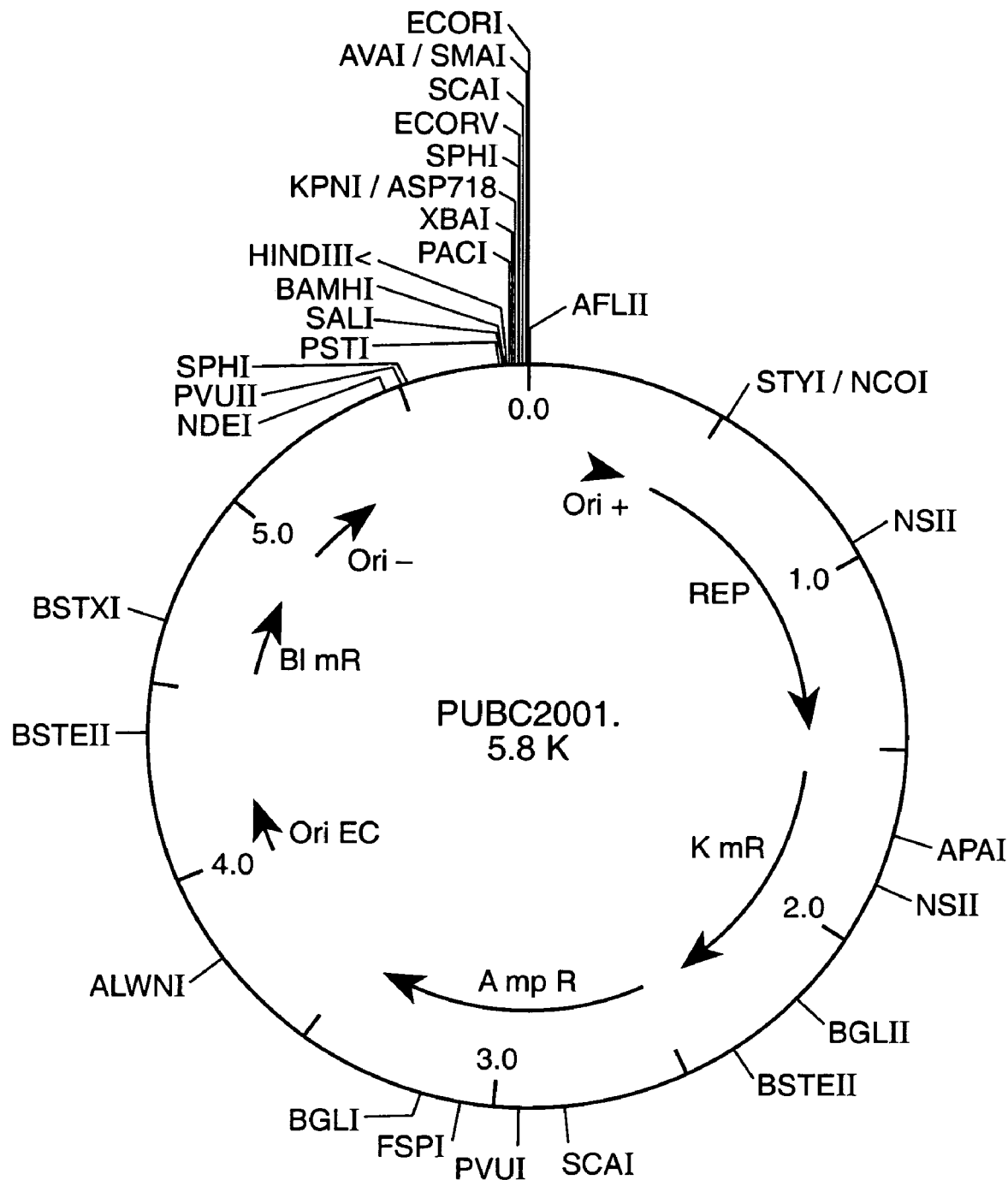
FIG._7

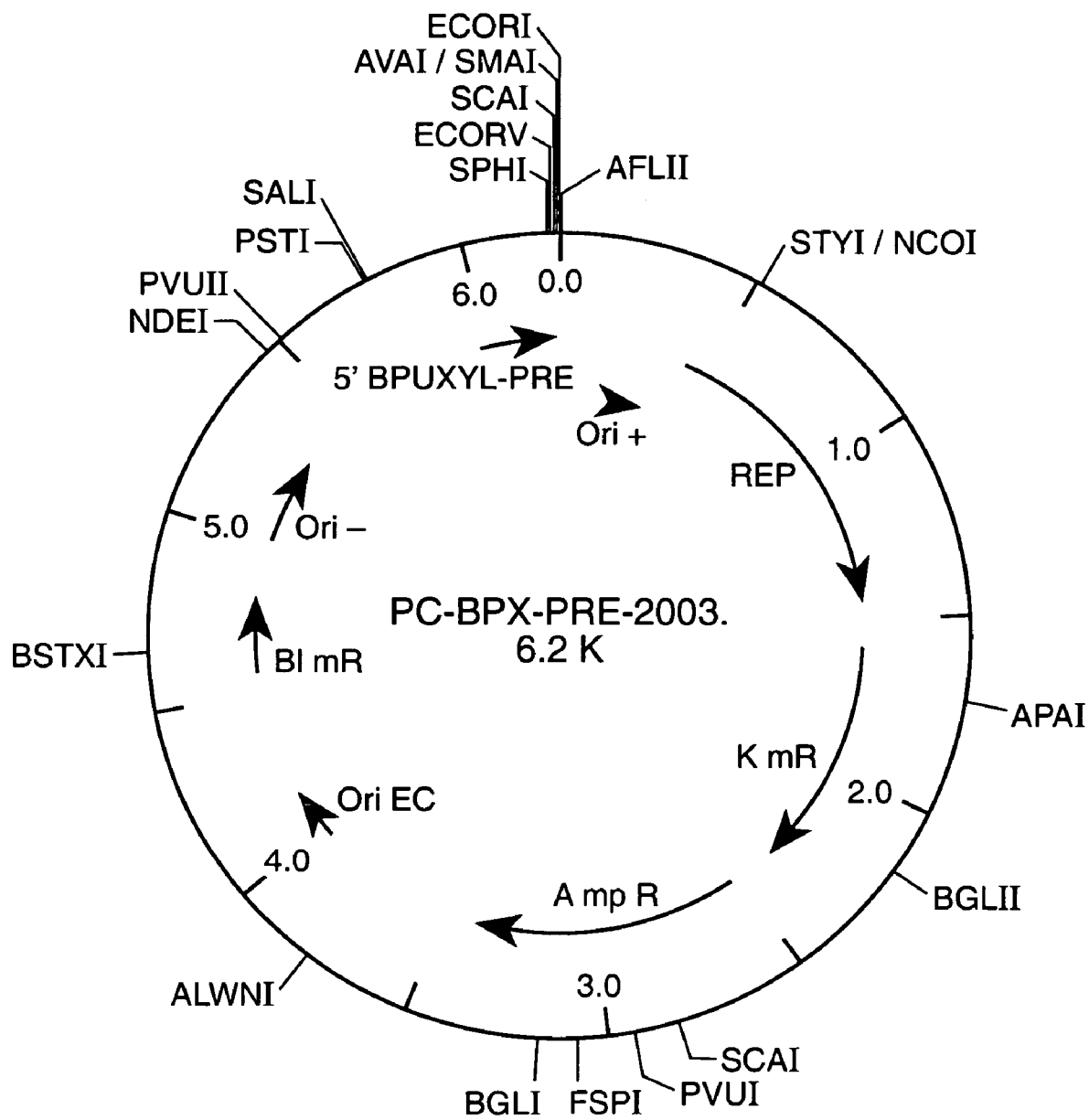
FIG._8

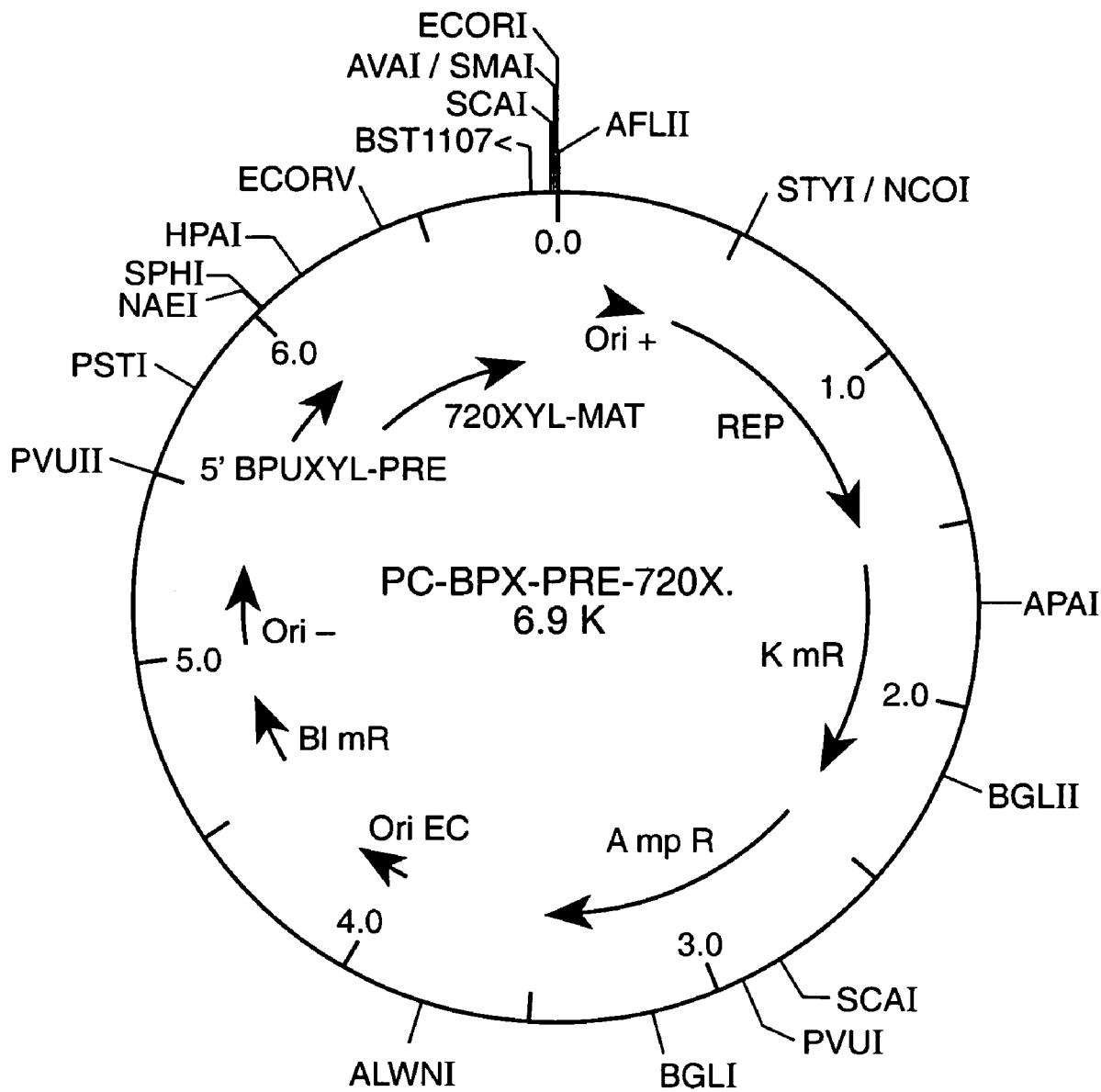
FIG._9

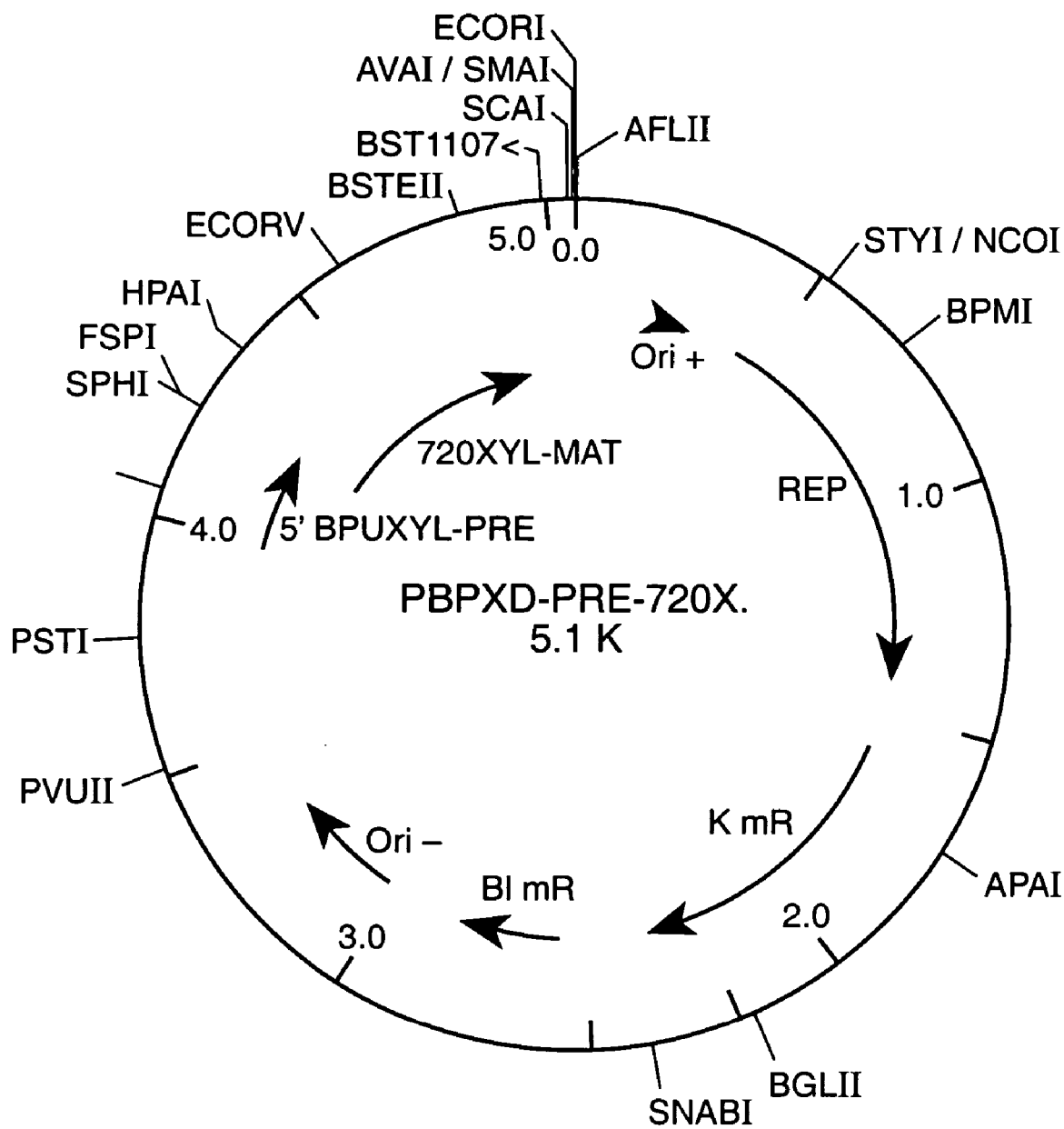
FIG._10

TCATGTAACT CGCCTTGATC TATTTCATTT GTATCAAAGG ATTTATACAC AAACAAGAGA
CATCCATGCC GGGTTAAAGC AGTATCGTTC CATCTAACAG AGAAGGNCTG CATGAAAGGA
GGTGATGGGT TTTTCATCTT AGGGATGACA GAACAATACG GATGAAAAAA GCAGAGGGAT
GGAAA

FIG._11

ATG AAT TTG AAA AGA TTG AGG CTG TTG TTT GTG ATG TGT ATT GGA TTT
Met Asn Leu Lys Arg Leu Arg Leu Leu Phe Val Met Cys Ile Gly Phe
 1            5                    10                   15

GTG CTG ACA CTG ACG GCT GTG CCG GCT CAT GCG
Val Leu Thr Leu Thr Ala Val Pro Ala His Ala
             20                  25

SEQUENCE LISTING

<160> NUMBER OF SEQ ID NOS: 29

<210> SEQ ID NO 1
<211> LENGTH: 663
<212> TYPE: DNA
<213> ORGANISM: Bacillus sp.

<400> SEQUENCE: 1

| | |
|---|---:|
| caaatcgtca ccgacaattc cattggcaac cacgatggct atgattatga attttggaaa | 60 |
| gatagcggtg gctctgggac aatgattctc aatcatggcg gtacgttcag tgcccaatgg | 120 |
| aacaatgtta acaacatatt attccgtaaa ggtaaaaaat tcaatgaaac acaaacacac | 180 |
| caacaagttg gtaacatgtc cataaactac ggagccaact tccaaccaaa tggtaatgcg | 240 |
| tatttatgcg tctatggttg gactgttgac cctcttgtcg aatattatat tgtcgacagt | 300 |
| tggggcaact ggcgtccacc aggagcaacg cctaagggga ccatcactgt tgatggagga | 360 |
| acatatgata tctacgagac tcttagagtc aatcaaccct ccattaaggg gattgccaca | 420 |
| tttaaacaat attggagtgt tcgaagatcg aaacgcacga gtggcacgat ttctgtcagc | 480 |
| aaccacttta gagcgtggga aaacttaggg atgaatatgg ggaaaatgta tgaagtcgcg | 540 |
| cttactgtag aaggctatca agtagcggga agtgctaatg tatatagcaa tacactaaga | 600 |
| attaacggta accctctctc aactattagt aatgacgaga gcataacttt ggataaaaac | 660 |
| aat | 663 |

<210> SEQ ID NO 2
<211> LENGTH: 663
<212> TYPE: DNA
<213> ORGANISM: Bacillus sp.
<220> FEATURE:
<221> NAME/KEY: CDS
<222> LOCATION: (1)...(663)
<220> FEATURE:
<221> NAME/KEY: mat_peptide
<222> LOCATION: (1)...(663)

<400> SEQUENCE: 2

| | |
|---|---:|
| caa atc gtc acc gac aat tcc att ggc aac cac gat ggc tat gat tat<br>Gln Ile Val Thr Asp Asn Ser Ile Gly Asn His Asp Gly Tyr Asp Tyr<br>1                  5                     10                  15 | 48 |
| gaa ttt tgg aaa gat agc ggt ggc tct ggg aca atg att ctc aat cat<br>Glu Phe Trp Lys Asp Ser Gly Gly Ser Gly Thr Met Ile Leu Asn His<br>                  20                     25                     30 | 96 |
| ggc ggt acg ttc agt gcc caa tgg aac aat gtt aac aac ata tta ttc<br>Gly Gly Thr Phe Ser Ala Gln Trp Asn Asn Val Asn Asn Ile Leu Phe<br>        35                     40                     45 | 144 |
| cgt aaa ggt aaa aaa ttc aat gaa aca caa aca cac caa caa gtt ggt<br>Arg Lys Gly Lys Lys Phe Asn Glu Thr Gln Thr His Gln Gln Val Gly<br>50                  55                     60 | 192 |
| aac atg tcc ata aac tac gga gcc aac ttc caa cca aat ggt aat gcg<br>Asn Met Ser Ile Asn Tyr Gly Ala Asn Phe Gln Pro Asn Gly Asn Ala<br>65                  70                     75                     80 | 240 |
| tat tta tgc gtc tat ggt tgg act gtt gac cct ctt gtc gaa tat tat<br>Tyr Leu Cys Val Tyr Gly Trp Thr Val Asp Pro Leu Val Glu Tyr Tyr<br>                  85                     90                     95 | 288 |
| att gtc gac agt tgg ggc aac tgg cgt cca cca gga gca acg cct aag<br>Ile Val Asp Ser Trp Gly Asn Trp Arg Pro Pro Gly Ala Thr Pro Lys<br>        100                     105                    110 | 336 |
| ggg acc atc act gtt gat gga gga aca tat gat atc tac gag act ctt | 384 |

```
Gly Thr Ile Thr Val Asp Gly Gly Thr Tyr Asp Ile Tyr Glu Thr Leu
        115                 120                 125 aga gtc aat caa ccc tcc att aag ggg att gcc aca ttt aaa caa tat        432
Arg Val Asn Gln Pro Ser Ile Lys Gly Ile Ala Thr Phe Lys Gln Tyr
130                 135                 140 tgg agt gtt cga aga tcg aaa cgc acg agt ggc acg att tct gtc agc        480
Trp Ser Val Arg Arg Ser Lys Arg Thr Ser Gly Thr Ile Ser Val Ser
145                 150                 155                 160 aac cac ttt aga gcg tgg gaa aac tta ggg atg aat atg ggg aaa atg        528
Asn His Phe Arg Ala Trp Glu Asn Leu Gly Met Asn Met Gly Lys Met
        165                 170                 175 tat gaa gtc gcg ctt act gta gaa ggc tat caa agt agc gga agt gct        576
Tyr Glu Val Ala Leu Thr Val Glu Gly Tyr Gln Ser Ser Gly Ser Ala
        180                 185                 190 aat gta tat agc aat aca cta aga att aac ggt aac cct ctc tca act        624
Asn Val Tyr Ser Asn Thr Leu Arg Ile Asn Gly Asn Pro Leu Ser Thr
        195                 200                 205 att agt aat gac gag agc ata act ttg gat aaa aac aat                    663
Ile Ser Asn Asp Glu Ser Ile Thr Leu Asp Lys Asn Asn
210                 215                 220

<210> SEQ ID NO 3
<211> LENGTH: 221
<212> TYPE: PRT
<213> ORGANISM: Bacillus sp.

<400> SEQUENCE: 3

Gln Ile Val Thr Asp Asn Ser Ile Gly Asn His Asp Gly Tyr Asp Tyr
1               5                   10                  15

Glu Phe Trp Lys Asp Ser Gly Ser Gly Thr Met Ile Leu Asn His
            20                  25                  30

Gly Gly Thr Phe Ser Ala Gln Trp Asn Asn Val Asn Asn Ile Leu Phe
        35                  40                  45

Arg Lys Gly Lys Lys Phe Asn Glu Thr Gln Thr His Gln Gln Val Gly
50                  55                  60

Asn Met Ser Ile Asn Tyr Gly Ala Asn Phe Gln Pro Asn Gly Asn Ala
65                  70                  75                  80

Tyr Leu Cys Val Tyr Gly Trp Thr Val Asp Pro Leu Val Glu Tyr Tyr
                85                  90                  95

Ile Val Asp Ser Trp Gly Asn Trp Arg Pro Pro Gly Ala Thr Pro Lys
            100                 105                 110

Gly Thr Ile Thr Val Asp Gly Gly Thr Tyr Asp Ile Tyr Glu Thr Leu
        115                 120                 125

Arg Val Asn Gln Pro Ser Ile Lys Gly Ile Ala Thr Phe Lys Gln Tyr
130                 135                 140

Trp Ser Val Arg Arg Ser Lys Arg Thr Ser Gly Thr Ile Ser Val Ser
145                 150                 155                 160

Asn His Phe Arg Ala Trp Glu Asn Leu Gly Met Asn Met Gly Lys Met
            165                 170                 175

Tyr Glu Val Ala Leu Thr Val Glu Gly Tyr Gln Ser Ser Gly Ser Ala
        180                 185                 190

Asn Val Tyr Ser Asn Thr Leu Arg Ile Asn Gly Asn Pro Leu Ser Thr
        195                 200                 205

Ile Ser Asn Asp Glu Ser Ile Thr Leu Asp Lys Asn Asn
210                 215                 220

<210> SEQ ID NO 4
```

-continued

<211> LENGTH: 744
<212> TYPE: DNA
<213> ORGANISM: Bacillus sp.

<400> SEQUENCE: 4

```
atgagacaaa agaaattgac gttgatttta gccttttag tttgttttgc actaacctta    60
cctgcagaaa taattcaggc acaaatcgtc accgacaatt ccattggcaa ccacgatggc   120
tatgattatg aattttggaa agatagcggt ggctctggga caatgattct caatcatggc   180
ggtacgttca gtgcccaatg gaacaatgtt aacaacatat tattccgtaa aggtaaaaaa   240
ttcaatgaaa cacaaacaca ccaacaagtt ggtaacatgt ccataaacta cggagccaac   300
ttccaaccaa atggtaatgc gtatttatgc gtctatggtt ggactgttga ccctcttgtc   360
gaatattata ttgtcgacag ttggggcaac tggcgtccac caggagcaac gcctaagggg   420
accatcactg ttgatggagg aacatatgat atctacgaga ctcttagagt caatcaaccc   480
tccattaagg ggattgccac atttaaacaa tattggagtg ttcgaagatc gaaacgcacg   540
agtggcacga tttctgtcag caaccacttt agagcgtggg aaaacttagg gatgaatatg   600
gggaaaatgt atgaagtcgc gcttactgta gaaggctatc aaagtagcgg aagtgctaat   660
gtatatagca atacactaag aattaacggt aaccctctct caactattag taatgacgag   720
agcataactt tggataaaaa caat                                         744
```

<210> SEQ ID NO 5
<211> LENGTH: 744
<212> TYPE: DNA
<213> ORGANISM: Bacillus sp.
<220> FEATURE:
<221> NAME/KEY: CDS
<222> LOCATION: (1)...(744)
<220> FEATURE:
<221> NAME/KEY: mat_peptide
<222> LOCATION: (1)...(744)
<220> FEATURE:
<221> NAME/KEY: sig_peptide
<222> LOCATION: (82)...(744)

<400> SEQUENCE: 5

```
atg aga caa aag aaa ttg acg ttg att tta gcc ttt tta gtt tgt ttt    48
Met Arg Gln Lys Lys Leu Thr Leu Ile Leu Ala Phe Leu Val Cys Phe
1               5                   10                  15 gca cta acc tta cct gca gaa ata att cag gca caa atc gtc acc gac    96
Ala Leu Thr Leu Pro Ala Glu Ile Ile Gln Ala Gln Ile Val Thr Asp
                20                  25                  30 aat tcc att ggc aac cac gat ggc tat gat tat gaa ttt tgg aaa gat   144
Asn Ser Ile Gly Asn His Asp Gly Tyr Asp Tyr Glu Phe Trp Lys Asp
            35                  40                  45 agc ggt ggc tct ggg aca atg att ctc aat cat ggc ggt acg ttc agt   192
Ser Gly Gly Ser Gly Thr Met Ile Leu Asn His Gly Gly Thr Phe Ser
        50                  55                  60 gcc caa tgg aac aat gtt aac aac ata tta ttc cgt aaa ggt aaa aaa   240
Ala Gln Trp Asn Asn Val Asn Asn Ile Leu Phe Arg Lys Gly Lys Lys
65                  70                  75                  80 ttc aat gaa aca caa aca cac caa caa gtt ggt aac atg tcc ata aac   288
Phe Asn Glu Thr Gln Thr His Gln Gln Val Gly Asn Met Ser Ile Asn
                85                  90                  95 tac gga gcc aac ttc caa cca aat ggt aat gcg tat tta tgc gtc tat   336
Tyr Gly Ala Asn Phe Gln Pro Asn Gly Asn Ala Tyr Leu Cys Val Tyr
                100                 105                 110 ggt tgg act gtt gac cct ctt gtc gaa tat tat att gtc gac agt tgg   384
Gly Trp Thr Val Asp Pro Leu Val Glu Tyr Tyr Ile Val Asp Ser Trp
```

-continued

```
                      115                 120                 125
ggc aac tgg cgt cca cca gga gca acg cct aag ggg acc atc act gtt      432
Gly Asn Trp Arg Pro Pro Gly Ala Thr Pro Lys Gly Thr Ile Thr Val
130                 135                 140 gat gga gga aca tat gat atc tac gag act ctt aga gtc aat caa ccc      480
Asp Gly Gly Thr Tyr Asp Ile Tyr Glu Thr Leu Arg Val Asn Gln Pro
145                 150                 155                 160 tcc att aag ggg att gcc aca ttt aaa caa tat tgg agt gtt cga aga      528
Ser Ile Lys Gly Ile Ala Thr Phe Lys Gln Tyr Trp Ser Val Arg Arg
                165                 170                 175 tcg aaa cgc acg agt ggc acg att tct gtc agc aac cac ttt aga gcg      576
Ser Lys Arg Thr Ser Gly Thr Ile Ser Val Ser Asn His Phe Arg Ala
            180                 185                 190 tgg gaa aac tta ggg atg aat atg ggg aaa atg tat gaa gtc gcg ctt      624
Trp Glu Asn Leu Gly Met Asn Met Gly Lys Met Tyr Glu Val Ala Leu
        195                 200                 205 act gta gaa ggc tat caa agt agc gga agt gct aat gta tat agc aat      672
Thr Val Glu Gly Tyr Gln Ser Ser Gly Ser Ala Asn Val Tyr Ser Asn
    210                 215                 220 aca cta aga att aac ggt aac cct ctc tca act att agt aat gac gag      720
Thr Leu Arg Ile Asn Gly Asn Pro Leu Ser Thr Ile Ser Asn Asp Glu
225                 230                 235                 240 agc ata act ttg gat aaa aac aat                                      744
Ser Ile Thr Leu Asp Lys Asn Asn
                245

<210> SEQ ID NO 6
<211> LENGTH: 248
<212> TYPE: PRT
<213> ORGANISM: Bacillus sp.

<400> SEQUENCE: 6

Met Arg Gln Lys Lys Leu Thr Leu Ile Leu Ala Phe Leu Val Cys Phe
1               5                   10                  15

Ala Leu Thr Leu Pro Ala Glu Ile Ile Gln Ala Gln Ile Val Thr Asp
            20                  25                  30

Asn Ser Ile Gly Asn His Asp Gly Tyr Asp Tyr Glu Phe Trp Lys Asp
        35                  40                  45

Ser Gly Gly Ser Gly Thr Met Ile Leu Asn His Gly Gly Thr Phe Ser
    50                  55                  60

Ala Gln Trp Asn Asn Val Asn Asn Ile Leu Phe Arg Lys Gly Lys Lys
65                  70                  75                  80

Phe Asn Glu Thr Gln Thr His Gln Gln Val Gly Asn Met Ser Ile Asn
                85                  90                  95

Tyr Gly Ala Asn Phe Gln Pro Asn Gly Asn Ala Tyr Leu Cys Val Tyr
            100                 105                 110

Gly Trp Thr Val Asp Pro Leu Val Glu Tyr Tyr Ile Val Asp Ser Trp
        115                 120                 125

Gly Asn Trp Arg Pro Pro Gly Ala Thr Pro Lys Gly Thr Ile Thr Val
    130                 135                 140

Asp Gly Gly Thr Tyr Asp Ile Tyr Glu Thr Leu Arg Val Asn Gln Pro
145                 150                 155                 160

Ser Ile Lys Gly Ile Ala Thr Phe Lys Gln Tyr Trp Ser Val Arg Arg
                165                 170                 175

Ser Lys Arg Thr Ser Gly Thr Ile Ser Val Ser Asn His Phe Arg Ala
            180                 185                 190

Trp Glu Asn Leu Gly Met Asn Met Gly Lys Met Tyr Glu Val Ala Leu
```

```
              195                 200                 205
Thr Val Glu Gly Tyr Gln Ser Ser Gly Ser Ala Asn Val Tyr Ser Asn
    210                 215                 220

Thr Leu Arg Ile Asn Gly Asn Pro Leu Ser Thr Ile Ser Asn Asp Glu
225                 230                 235                 240

Ser Ile Thr Leu Asp Lys Asn Asn
            245

<210> SEQ ID NO 7
<211> LENGTH: 81
<212> TYPE: DNA
<213> ORGANISM: Bacillus sp.

<400> SEQUENCE: 7
atgagacaaa agaaattgac gttgatttta gccttttag tttgttttgc actaaccta     60 cctgcagaaa taattcaggc a                                             81

<210> SEQ ID NO 8
<211> LENGTH: 81
<212> TYPE: DNA
<213> ORGANISM: Bacillus sp.
<220> FEATURE:
<221> NAME/KEY: CDS
<222> LOCATION: (1)...(81)
<220> FEATURE:
<221> NAME/KEY: sig_peptide
<222> LOCATION: (1)...(81)

<400> SEQUENCE: 8 atg aga caa aag aaa ttg acg ttg att tta gcc ttt tta gtt tgt ttt    48
Met Arg Gln Lys Lys Leu Thr Leu Ile Leu Ala Phe Leu Val Cys Phe
 1               5                  10                  15 gca cta acc tta cct gca gaa ata att cag gca                        81
Ala Leu Thr Leu Pro Ala Glu Ile Ile Gln Ala
             20                  25

<210> SEQ ID NO 9
<211> LENGTH: 27
<212> TYPE: PRT
<213> ORGANISM: Bacillus sp.

<400> SEQUENCE: 9

Met Arg Gln Lys Lys Leu Thr Leu Ile Leu Ala Phe Leu Val Cys Phe
 1               5                  10                  15

Ala Leu Thr Leu Pro Ala Glu Ile Ile Gln Ala
             20                  25

<210> SEQ ID NO 10
<211> LENGTH: 1513
<212> TYPE: DNA
<213> ORGANISM: Bacillus sp.

<400> SEQUENCE: 10
aaattgaatt gtgtatatct aatgataacg acaaatcgtc actgttttta aactaatctc    60
aaaccaatac ttctttattt aacgctaacc acttgcaatc ttatcacaag aacattcttt   120
ataggaactt tcccattttgc aagacgataa aaaatctttt tcccctattt tatcttatcg   180
ccttgatcgg tttaatttgt aaactttatt ttagttacg tgatgttccc tcattcatac    240
cattaatcac agttaacgct agagtcatct ttttcggtt ctcaaaaata cctgaagaac    300
atttatgtca tattttctca cgccgctcca taatggaata tatatactct tttatacata   360
```

```
ttaagtaaat tagtatatac ttgcgttatc aaaatgtgag ataatctaat tgatcaaaca    420
agcagctatc caaaaaacac tgatgttgac ctcttaaaga agtgtcacta tctatgaaaa    480
gataattatc cagtttcaaa atttgaaata gtgtgtatgg aatagtttga atgtcaactg    540
ctgtgaaagg agggtaggta gtaccgtaga cttcattacc aaaaattagt tgtaaaaaaa    600
ttaaaaggag gaatgcctaa tgagacaaaa gaaattgacg ttgattttag cctttttagt    660
ttgttttgca ctaaccttac ctgcagaaat aattcaggca caaatcgtca ccgacaattc    720
cattggcaac cacgatggct atgattatga attttggaaa gatagcggtg gctctgggac    780
aatgattctc aatcatggcg gtacgttcag tgcccaatgg aacaatgtta caacatatt     840 attccgtaaa ggtaaaaaat tcaatgaaac acaaacacac caacaagttg gtaacatgtc    900
cataaactac ggagccaact tccaaccaaa tggtaatgcg tatttatgcg tctatggttg    960
gactgttgac cctcttgtcg aatattatat tgtcgacagt tggggcaact ggcgtccacc   1020
aggagcaacg cctaagggga ccatcactgt tgatggagga acatatgata tctacgagac   1080
tcttagagtc aatcaaccct ccattaaggg gattgccaca tttaaacaat attggagtgt   1140
tcgaagatcg aaacgcacga gtggcacgat ttctgtcagc aaccacttta gagcgtggga   1200
aaacttaggg atgaatatgg ggaaaatgta tgaagtcgcg cttactgtag aaggctatca   1260
aagtagcgga agtgctaatg tatatagcaa tacactaaga attaacggta accctctctc   1320
aactattagt aatgacgaga gcataacttt ggataaaaac aattaaaaat ccttatctct   1380
ttcggttcag ttctcattat tttcaaataa cctcccggtt ggatcttttc caacgggagg   1440
ttttattgga aaggttaagt atagtatact ccgattccat ccagaggaat gcttgaaaca   1500
cctccgtcac tag                                                      1513

<210> SEQ ID NO 11
<211> LENGTH: 1513
<212> TYPE: DNA
<213> ORGANISM: Bacillus sp.
<220> FEATURE:
<221> NAME/KEY: CDS
<222> LOCATION: (620)...(1363)
<220> FEATURE:
<221> NAME/KEY: mat_peptide
<222> LOCATION: (701)...(1363)
<220> FEATURE:
<221> NAME/KEY: sig_peptide
<222> LOCATION: (620)...(700)

<400> SEQUENCE: 11
aaattgaatt gtgtatatct aatgataacg acaaatcgtc actgttttta aactaatctc     60
aaaccaatac ttctttattt aacgctaacc acttgcaatc ttatcacaag aacattcttt    120
ataggaactt tcccatttgc aagacgataa aaaatctttt tcccctattt tatcttatcg    180
ccttgatcgg tttaatttgt aaactttatt ttagtttacg tgatgttccc tcattcatac    240
cattaatcac agttaacgct agagtcatct tttttcggtt ctcaaaaata cctgaagaac    300
atttatgtca tattttctca cgccgctcca taatggaata tatatactct tttatacata    360
ttaagtaaat tagtatatac ttgcgttatc aaaatgtgag ataatctaat tgatcaaaca    420
agcagctatc caaaaaacac tgatgttgac ctcttaaaga agtgtcacta tctatgaaaa    480
gataattatc cagtttcaaa atttgaaata gtgtgtatgg aatagtttga atgtcaactg    540
ctgtgaaagg agggtaggta gtaccgtaga cttcattacc aaaaattagt tgtaaaaaaa    600
ttaaaaggag gaatgccta atg aga caa aag aaa ttg acg ttg att tta gcc    652
                     Met Arg Gln Lys Lys Leu Thr Leu Ile Leu Ala
```

-continued

```
                     1               5                  10
ttt tta gtt tgt ttt gca cta acc tta cct gca gaa ata att cag gca       700
Phe Leu Val Cys Phe Ala Leu Thr Leu Pro Ala Glu Ile Ile Gln Ala
                 15                  20                  25 caa atc gtc acc gac aat tcc att ggc aac cac gat ggc tat gat tat       748
Gln Ile Val Thr Asp Asn Ser Ile Gly Asn His Asp Gly Tyr Asp Tyr
                 30                  35                  40 gaa ttt tgg aaa gat agc ggt ggc tct ggg aca atg att ctc aat cat       796
Glu Phe Trp Lys Asp Ser Gly Gly Ser Gly Thr Met Ile Leu Asn His
     45                  50                  55 ggc ggt acg ttc agt gcc caa tgg aac aat gtt aac aac ata tta ttc       844
Gly Gly Thr Phe Ser Ala Gln Trp Asn Asn Val Asn Asn Ile Leu Phe
 60                  65                  70                  75 cgt aaa ggt aaa aaa ttc aat gaa aca caa aca cac caa caa gtt ggt       892
Arg Lys Gly Lys Lys Phe Asn Glu Thr Gln Thr His Gln Gln Val Gly
                 80                  85                  90 aac atg tcc ata aac tac gga gcc aac ttc caa cca aat ggt aat gcg       940
Asn Met Ser Ile Asn Tyr Gly Ala Asn Phe Gln Pro Asn Gly Asn Ala
                 95                 100                 105 tat tta tgc gtc tat ggt tgg act gtt gac cct ctt gtc gaa tat tat       988
Tyr Leu Cys Val Tyr Gly Trp Thr Val Asp Pro Leu Val Glu Tyr Tyr
            110                 115                 120 att gtc gac agt tgg ggc aac tgg cgt cca cca gga gca acg cct aag      1036
Ile Val Asp Ser Trp Gly Asn Trp Arg Pro Pro Gly Ala Thr Pro Lys
            125                 130                 135 ggg acc atc act gtt gat gga gga aca tat gat atc tac gag act ctt      1084
Gly Thr Ile Thr Val Asp Gly Gly Thr Tyr Asp Ile Tyr Glu Thr Leu
140                 145                 150                 155 aga gtc aat caa ccc tcc att aag ggg att gcc aca ttt aaa caa tat      1132
Arg Val Asn Gln Pro Ser Ile Lys Gly Ile Ala Thr Phe Lys Gln Tyr
                160                 165                 170 tgg agt gtt cga aga tcg aaa cgc acg agt ggc acg att tct gtc agc      1180
Trp Ser Val Arg Arg Ser Lys Arg Thr Ser Gly Thr Ile Ser Val Ser
            175                 180                 185 aac cac ttt aga gcg tgg gaa aac tta ggg atg aat atg ggg aaa atg      1228
Asn His Phe Arg Ala Trp Glu Asn Leu Gly Met Asn Met Gly Lys Met
            190                 195                 200 tat gaa gtc gcg ctt act gta gaa ggc tat caa agt agc gga agt gct      1276
Tyr Glu Val Ala Leu Thr Val Glu Gly Tyr Gln Ser Ser Gly Ser Ala
205                 210                 215 aat gta tat agc aat aca cta aga att aac ggt aac cct ctc tca act      1324
Asn Val Tyr Ser Asn Thr Leu Arg Ile Asn Gly Asn Pro Leu Ser Thr
220                 225                 230                 235 att agt aat gac gag agc ata act ttg gat aaa aac aat taaaaatcct      1373
Ile Ser Asn Asp Glu Ser Ile Thr Leu Asp Lys Asn Asn
                240                 245 tatctctttc ggttcagttc tcattatttt caaataacct cccggttgga tcttttccaa   1433
cgggaggttt tattggaaag gttaagtata gtatactccg attccatcca gaggaatgct   1493
tgaaacacct ccgtcactag                                               1513

<210> SEQ ID NO 12
<211> LENGTH: 619
<212> TYPE: DNA
<213> ORGANISM: Bacillus sp.

<400> SEQUENCE: 12
aaattgaatt gtgtatatct aatgataacg acaaatcgtc actgttttta aactaatctc      60
aaaccaatac ttctttattt aacgctaacc acttgcaatc ttatcacaag aacattcttt     120
```

```
ataggaactt tcccatttgc aagacgataa aaaatctttt tccccctattt tatcttatcg      180 ccttgatcgg tttaatttgt aaactttatt ttagtttacg tgatgttccc tcattcatac      240
cattaatcac agttaacgct agagtcatct tttttcggtt ctcaaaaata cctgaagaac      300
atttatgtca tattttctca cgccgctcca taatggaata tatatactct tttatacata      360
ttaagtaaat tagtatatac ttgcgttatc aaaatgtgag ataatctaat tgatcaaaca      420
agcagctatc caaaaaacac tgatgttgac ctcttaaaga agtgtcacta tctatgaaaa      480
gataattatc cagtttcaaa atttgaaata gtgtgtatgg aatagtttga atgtcaactg      540
ctgtgaaagg agggtaggta gtaccgtaga cttcattacc aaaaattagt tgtaaaaaaa      600
ttaaaaggag gaatgccta                                                  619
```

```
<210> SEQ ID NO 13
<211> LENGTH: 150
<212> TYPE: DNA
<213> ORGANISM: Bacillus sp.

<400> SEQUENCE: 13
taaaaatcct tatctctttc ggttcagttc tcattatttt caaataacct cccggttgga       60
tcttttccaa cgggaggttt tattggaaag gttaagtata gtatactccg attccatcca      120
gaggaatgct tgaaacacct ccgtcactag                                       150
```

```
<210> SEQ ID NO 14
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 14
cccccctacg tagcggccgc cccggccggt aacctaggaa gtcagcgccc tgcacc           56
```

```
<210> SEQ ID NO 15
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 15
cccccctacg taggccgggg cggccgcggt tacctagggc ctcgtgatac gcctat           56
```

```
<210> SEQ ID NO 16
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 16
acgaggaaag atgctgttct tgtaaatgag t                                      31
```

```
<210> SEQ ID NO 17
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 17
```
taccttgtct acaaacccc                                               19

<210> SEQ ID NO 18
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 18
cggtcgccgc atacacta                                                18

<210> SEQ ID NO 19
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 19 ccccccccccg gtaacctgca ttaatgaatc ggccaa                            36

<210> SEQ ID NO 20
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 20 ccccccccccg gttaccgtat ttattaactt ctcctagta                         39

<210> SEQ ID NO 21
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 21 ccccccctcta gattaattaa ccaagcttgg gatccgtcga cctgcagatc             50

<210> SEQ ID NO 22
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 22 ccccccctgaa atcagctgga ctaaaaggga tgcaatttc                         39

<210> SEQ ID NO 23
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 23
ccccccgtcg accgcatgcg ccggcacagc                                   30

<210> SEQ ID NO 24
<211> LENGTH: 39
<212> TYPE: DNA
<213> ORGANISM: Artificial Sequence -continued

```
<220> FEATURE:
<223> OTHER INFORMATION: synthetic oligonucleotide

<400> SEQUENCE: 24 cccccgcat gcgcaaatcg tcaccgacaa ttccattgg                                39

<210> SEQ ID NO 25
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 25
taccttgtct acaaacccc                                                     19

<210> SEQ ID NO 26
<211> LENGTH: 185
<212> TYPE: DNA
<213> ORGANISM: Bacillus pumilus
<220> FEATURE:
<221> NAME/KEY: misc_feature
<222> LOCATION: (1)...(185)
<223> OTHER INFORMATION: n = A,T,C or G

<400> SEQUENCE: 26
tcatgtaact cgccttgatc tatttcattt gtatcaaagg atttatacac aaacaagaga        60
catccatgcc gggttaaagc agtatcgttc catctaacag agaaggnctg catgaaagga       120
ggtgatgggt ttttcatctt agggatgaca gaacaatacg gatgaaaaaa ggagagggat       180
ggaaa                                                                  185

<210> SEQ ID NO 27
<211> LENGTH: 81
<212> TYPE: DNA
<213> ORGANISM: Bacillus pumilus

<400> SEQUENCE: 27
atgaatttga aaagattgag gctgttgttt gtgatgtgta ttggatttgt gctgacactg        60
acggctgtgc cggctcatgc g                                                  81

<210> SEQ ID NO 28
<211> LENGTH: 81
<212> TYPE: DNA
<213> ORGANISM: Bacillus pumilus
<220> FEATURE:
<221> NAME/KEY: CDS
<222> LOCATION: (1)...(81)

<400> SEQUENCE: 28 atg aat ttg aaa aga ttg agg ctg ttg ttt gtg atg tgt att gga ttt         48
Met Asn Leu Lys Arg Leu Arg Leu Leu Phe Val Met Cys Ile Gly Phe
 1               5                  10                  15 gtg ctg aca ctg acg gct gtg ccg gct cat gcg                              81
Val Leu Thr Leu Thr Ala Val Pro Ala His Ala
            20                  25

<210> SEQ ID NO 29
<211> LENGTH: 27
<212> TYPE: PRT
<213> ORGANISM: Bacillus pumilus

<400> SEQUENCE: 29

Met Asn Leu Lys Arg Leu Arg Leu Leu Phe Val Met Cys Ile Gly Phe
```

-continued

```
 1               5              10              15
Val Leu Thr Leu Thr Ala Val Pro Ala His Ala
            20              25
```

XYLANASE, MICROORGANISMS PRODUCING IT, DNA MOLECULES, METHODS FOR PREPARING THIS XYLANASE AND USES OF THE LATTER

This is a divisional of application Ser. No. 09/909,207 filed Jul. 19, 2001 now U.S. Pat. No. 7,022,827.

The invention relates to a new xylanase. The invention also relates to the methods for preparing this xylanase, to the uses of the latter and to compositions comprising it.

The invention also relates to a new strain of microorganisms producing this xylanase and to a DNA molecule comprising the nucleotide sequence which codes for this xylanase. The invention also relates to vectors containing this DNA molecule and to strains transformed by these vectors.

The invention also relates to the promoter derived from the gene which codes for *Bacillus pumilus* PRL B12 xylanase and the presequence which codes for the signal peptide of *Bacillus pumilus* PRL B12 xylanase. The invention also relates to vectors which contain this promoter and this presequence, and also to the DNA molecule comprising the nucleotide sequence which codes for the mature portion of the xylanase of the invention. The invention also relates to strains transformed by these vectors.

Thermostable xyalanases which are active over a wide pH range are known, such as, in particular, xylanases produced by strains of alkalophilic *bacillus* (Gupta et al. Biotechnology Letters, 1992, 14 (11), pages 1045-1046 and International Patent Application WO 94/04664). However, despite these properties, these enzymes would appear to be poorly effective in bleaching paper pulp.

Consequently, there is at present a need for a xylanase which can be used in the treatment of paper pulp, which is very stable and also very active over a wide range of temperature and of basic and acid pH.

The object of the present invention is to provide a new xylanase which is active over a wide pH range, both at alkaline pH and at acid pH.

The object of the present invention is also to identify, isolate and provide a strain, especially a *Bacillus* strain, which produces the said xylanase naturally.

The object of the present invention is also to isolate and provide a DNA molecule comprising a nucleotide sequence which codes for the said xylanase.

The object of the present invention is also to prepare and provide an expression vector containing the nucleotide sequence coding for the said xylanase.

The object of the present invention is also to prepare and provide an integration vector containing the nucleotide sequence coding for the said xylanase.

The object of the present invention is also to prepare and provide the promoter drived from the gene which codes for *Bacillus pumilus* PRL B12 xylanase. The object of the present invention is also to prepare and provide the presequence which codes for the signal peptide of *Bacillus pumilus* PRL B12 xylanase. The vectors which comprise this promoter and/or this presequence also contain the DNA molecule comprising the nucleotide sequence which codes for the mature portion of the xylanase of the invention. The strains transformed by these vectors produce the xylanase of the invention heterologously.

The object of the present invention is also to prepare and provide a *Bacillus* host transformed with the expression vector which contains the DNA molecule comprising the nucleotide sequence of, the *Bacillus* strain coding for the said xylanase.

The object of the present invention is also to prepare and provide a *Bacillus* host transformed with the expression vector which contains the DNA molecule comprising the nucleotide sequence of the *Bacillus* strain coding for the said xylanase [sic].

The object of the present invention is also to prepare and provide a composition containing this xylanase.

The object of the present invention is also to prepare and provide a xylanase which can be used in the treatment of paper pulp, and pulps having a basic, neutral or acid pH, and in particular pulps having an especially basic pH and paper pulps of various origins, such as the pulps originating from coniferous trees, the pulps originating from broad-leaved trees and especially eucalyptus pulp.

To this end, the invention relates to a xylanase originating from a *Bacillus*, and more especially from an aerobic and non-thermophilic microorganism.

It is preferable to use *Bacillus* sp. strain 720/1 or a derivative or mutant of this strain. The xylanase of the invention is derived from (naturally produced by) *Bacillus* sp. strain 720/1. Xylanase is classified in the international system under the EC number 3.2.1.8. It is an endo-1,4-beta-xylanase.

Preferably, the isolated and purified xylanase consists of a single type of polypeptide having a molecular weight of approximately 25 kDa.

The invention relates to an isolated and purified xylanase comprising the amino acid sequence from 1 to 221 amino acids (SEQ ID NO:3) or a modified sequence derived from this sequence. The amino acid sequence and the nucleotide sequence (SEQ ID NO:1) coding for the mature xylanase, together with its translation into amino acids (SEQ ID NO:2), is given in FIG. 1 (FIGS. 1a and 1b).

The xylanase of the invention is synthesized in the form of a precursor. The precursor contains 248 amino acids: (SEQ ID NO:6). The nucleotide sequence SEQ ID NO:4) coding for the xylanase precursor, as well as its translation into amino acids (SEQ ID NO:5), are identified.

The precursor contains the sequence of 221 amino acids (SEQ ID NO:3) of the mature xylanase and the sequence of 27 amino acids (SEQ ID NO:9) of the presequence.

The mature xylanase sequence is preceded by a presequence. The latter is an additional sequence of 27 amino acids (SEQ ID NO:9). The corresponding nucleotide sequence (SEQ ID NO:7), as well as its translation into amino acids (SEQ ID NO:8), are identified. This presequence codes for the signal peptide of the xylanase of the invention.

As a special preference, the said xylanase has a determined isoelectric point of between approximately 9.5 and approximately 9.7.

The xylanase according to the invention is thermostable and active over a wide pH range. Preferably, the xylanase according to the invention is alkaline.

The xylanase according to the invention possesses, moreover, all appropriate properties compatible with the actual industrial conditions of enzyme treatment of paper pulp. According to the numerous steps of the various treatments of paper pulp employed industrially, these properties are good stability with respect to pH and temperature, and enzyme activity over a wide range of pH and temperature, such as, in particular, a pH of between approximately 5 and 10 and a temperature of between approximately 50 and 80° C.

The xylanase of the invention is active over a range of pH above or equal to approximately 5. The xylanase of the invention is active over a range of pH lower or equal to approximately 11. The xylanase develops an enzyme activity of more than 50% of the maximal activity, measured at a temperature of approximately 50° C. and in the presence of xylan, over a range of pH above or equal to approximately 5.0. The xylanase develops an enzyme activity of more than 50% of the maximal activity, measured at a temperature of approximately 50° C. and in the presence of xylan, over a pH range below approximately 10.5.

The xylanase of the invention is active over a range of temperature above or equal to approximately 50° C. The xylanase of the invention is active over a range of temperature below or equal to approximately 80° C. The xylanase develops an enzyme activity of more than 50% of the maximal activity, measured at a pH of approximately 9 and in the presence of xylan, over a range of temperature above or equal to approximately 50° C. The xylanase develops an enzyme activity of more than 50% of the maximal activity, measured at a pH of approximately 9 and in the presence of xylan, over a temperature range below approximately 80° C.

The invention also relates to a modified xylanase, that is to say an enzyme whose amino acid sequence differs from that of the wild-type enzyme by at least one amino acid. These modifications may be obtained by standard mutagenesis techniques on the DNA, such as exposure to ultraviolet radiation or to chemical products such as ethyl methanesulphonate (EMS), N-methyl-N-nitro-N-nitrosoguanidine (MNNG), sodium nitrite or O-methylhydroxylamine, or by genetic engineering techniques such as, for example, site-directed mutagenesis or random mutagenesis. These techniques are known to a person skilled in the art and are described, in particular, in Molecular Cloning—a laboratory manual—Sambrook, Fritsch, Maniatis—second edition, 1989, Chapter 15.

The invention also relates to a xylanase having immunochemical properties identical or partially identical to the xylanase obtained from *Bacillus* sp. strain 720/1. The immunochemical properties may be determined immunologically by tests of identity, in particular using specific polyclonal or monoclonal antibodies. Tests of identity are known to a person skilled in the art, such as, in particular, the Ouchterlony immunodiffusion method or the immunoelectrophoresis method. Examples of such methods are described by Axelsen N. H., Handbook of Immunoprecipitation Gel Techniques, Blackwell Scientific Publications, 1983, Chapters 5 and 14; the terms "antigenic identity" and "partial antigenic identity" are described in this document in Chapters 5, 19 and 20. A serum containing the specific antibody is prepared according to the method described, by immunizing animals (for example mice, rabbits or goats) with a purified xylanase preparation. This preparation may be mixed with an additive such as Freund's adjuvant, and the mixture obtained is injected into animals. The polyclonal antibody is obtained after one or several immunizations. An example consists in injecting subcutaneously at two-week intervals four fractions each containing 150 micrograms of purified xylanase; the immunization then lasts 8 weeks. The serum is withdrawn after the immunization period and the immunoglobulin may be isolated according to the method described by Axelsen N. H. (1983).

The present invention also relates to the identification and provision of a new, isolated and purified aerobic bacterium producing xylanase. Generally, it belongs to the family Bacillaceae. Preferably, it belongs to the genus *Bacillus*. As a special preference, the said *Bacillus* is *Bacillus* sp. strain 720/1 or a derivative or mutant of this strain.

Derivative of this strain is understood to mean any naturally modified bacterium. The derivatives of this strain may be obtained by known modification techniques such as culture on specific medium, ultraviolet radiation or X-rays. Mutant of this strain is understood to mean any artificially modified bacterium. The mutants of this strain may be obtained by known modification techniques such as exposure to mutagenic agents and genetic engineering techniques. These techniques are known to a person skilled in the art and are described, in particular, in Sambrook et al., 1989, Chapter 15.

*Bacillus* sp. strain 720/1 was deposited at the collection named Belgian Coordinated Collections of Microorganisms (LMG culture collection, Ghent University, Microbiology Laboratory—K. L. Ledeganckstraat 35, B-9000 Ghent, Belgium) in accordance with the Budapest Treaty under the number LMG P-14798 on 9 Jun. 1994. The invention relates to an isolated and purified culture of *Bacillus* sp. strain 720/1 and to a derived or mutated culture of the latter.

The strain of the present invention was identified by its biochemical features: aerobic Gram-positive bacterium which takes the form of a rod; it forms an endospore. It is oligosporogenous.

The invention also relates to the isolation and provision of a DNA molecule comprising the nucleotide sequence (SEQ ID NO:1) which codes for the mature xylanase of *Bacillus* sp. 720/1 (LMG P-14798) or a modified sequence derived from this sequence. Preferably, this DNA molecule comprises the entire *Bacillus* sp. 720/1 xylanase gene. Entire xylanase gene (SEQ ID NO:10) is understood to mean at least the transcription promoter(s), the signal sequence(s), the nucleotide sequence coding for the mature xylanase and the transcription terminator(s).

Modified sequence derived from the DNA molecule is understood to mean any DNA molecule obtained by modification of one or more nucleotides of the gene which codes for the xylanase of the invention. The techniques of obtaining such sequences are known to a person skilled in the art, and are described, in particular, in Molecular Cloning—a laboratory manual—Sambrook, Fritsch, Maniatis—second edition, 1989, Chapter 15. Usually, the modified sequence derived from the DNA molecule comprises at least 70% homology with the nucleotide sequences [sic] (SEQ ID NO:1) of the gene which codes for the xylanase of the invention, that is to say at least 70% of identical nucleotides having the same position in the sequence. Preferably, the modified sequence derived from the DNA molecule comprises at least 80% homology with the nucleotide sequence (SEQ ID NO:1) of the gene which codes for the xylanase of the invention. As a special preference, the modified sequence derived from the DNA molecule comprises at least 90% homology with the nucleotide sequences [sic] (SEQ ID NO:1) of the gene which codes for the xylanase of the invention.

The complete nucleotide sequence coding for the mature xylanase, together with its translation into amino acids (SEQ ID NO:2), is given in FIG. 1 (FIGS. 1*a* and 1*b*).

Usually, the DNA molecule according to the invention comprises at least the nucleotide sequence (SEQ ID NO:4) which codes for the xylanase precursor or a modified sequence derived from this sequence. This nucleotide sequence (SEQ ID NO:4) comprises the nucleotide sequence (SEQ ID NO:1) coding for the mature xylanase of *Bacillus* sp. 720/1 (LMG P-14798) and its signal sequence (presequence) (SEQ ID NO:7). Preferably, this DNA molecule comprises the entire *Bacillus* sp. 720/1 xylanase gene and, as a special preference, the nucleotide sequence (SEQ ID NO:10). The nucleotide sequence (SEQ ID NO:10) consists, in the aminocarboxy direction and from left to right, of the nucleotide sequence (SEQ ID NO:12) which comprises the xylanase promoter, the nucleotide sequence of the presequence (SEQ ID NO:7), the nucleotide sequence of the mature xylanase (SEQ ID NO:1) and the nucleotide sequence (SEQ ID NO:13) which comprises the xylanase terminator. FIG. 2

(FIG. 2a and FIG. 2b) shows the nucleotide sequence of the gene coding for the xylanase, together with its translation into amino acids (SEQ ID NO:11).

In a variant, the invention also relates to a DNA molecule which comprises the promoter derived from the gene which codes for *Bacillus pumilus* PRL B12 xylanase, a presequence and the nucleotide sequence (SEQ ID NO:1) which codes for *Bacillus* sp. 720/1 xylanase or a modified sequence derived from this sequence. In another variant, the invention also relates to a DNA molecule which comprises a promoter, the presequence which codes for the signal peptide of *Bacillus pumilus* PRL B12 xylanase and the nucleotide sequence (SEQ ID NO:1) which codes for *Bacillus* sp. 720/1 xylanase or a modified sequence derived from this sequence. Preferably, the invention relates to a DNA molecule which comprises the promoter (SEQ ID NO:26) derived from the gene which codes for *Bacillus pumilus* PRL B12 xylanase, the presequence (SEQ ID NO:27) which codes for the signal peptide of *Bacillus pumilus* PRL B12 xylanase and the nucleotide sequence (SEQ ID NO:1) which codes for *Bacillus* sp. 720/1 xylanase or a modified sequence derived from this sequence.

The invention also relates to the promoter (SEQ ID NO:26) derived from the gene which codes for *Bacillus pumilus* PRL B12 xylanase. The sequence of the promoter is illustrated in FIG. 11.

The invention also relates to the presequence (SEQ ID NO:27) which codes for the signal peptide of *Bacillus pumilus* PRL B12 xylanase. The corresponding sequence of 27 amino acids has been identified (SEQ ID NO:29). This nucleotide sequence, together with its translation into amino acids (SEQ ID NO:28), is illustrated in FIG. 12.

The method for obtaining and preparing the promoter derived from the gene which codes for *Bacillus pumilus* PRL B12 xylanase and of the presequence which codes for the signal peptide of *Bacillus pumilus* PRL B12 xylanase is described in Example 17 and in FIG. 1 of European Patent Application 0,634,490, which is incorporated by reference in this application.

*Bacillus pumilus* strain PRL B12 was deposited at the ATCC collection (American Type Culture Collection, 12301 Parklawn Drive, Rockville, Md., 20852, USA) in accordance with the Budapest Treaty under the number ATCC 55443 on 24 Jun. 1993.

The invention also relates to a mutated DNA molecule, and to the mutated xylanase derived therefrom (for which the mutated DNA molecule codes), obtained by modification of the nucleotide sequence of the gene which codes for the xylanase defined above. The techniques of obtaining such mutated xylanases are known to a person skilled in the art and are described, in particular, in Molecular Cloning—a laboratory manual—Sambrook, Fritsch, Maniatis—second edition, 1989, Chapter 15.

The present invention also relates to an expression vector or chromosomal integration vector containing a DNA molecule as defined above. Generally, the expression vector or the chromosomal integration vector contains the DNA molecule which comprises the nucleotide sequence (SEQ ID NO:1) which codes for *Bacillus* sp. 720/1 xylanase or a modified sequence derived from this sequence. Usually, the expression vector or the chromosomal integration vector contains a DNA molecule which comprises the gene which codes for the xylanase or a modified sequence derived from this sequence. Preferably, the expression vector or the chromosomal integration vector contains the DNA molecule which comprises the nucleotide sequence (SEQ ID NO:10) which codes for *Bacillus* sp. 720/1 xylanase or a modified sequence derived from this sequence. As a special preference, this vector is the expression vector pUBRD-720X11. Good results have also been obtained with the expression vector pUBR-720X11.

A variant of the invention relates to an expression vector or a chromosomal integration vector which contains a DNA molecule comprising the gene which codes for the mature portion of the xylanase or a modified sequence derived from this molecule. Generally, the expression vector or the chromosomal integration vector contains the DNA molecule which comprises the nucleotide sequence (SEQ ID NO:1) which codes for *Bacillus* sp. 720/1 xylanase or a modified sequence derived from this sequence. Usually, the expression vector or the chromosomal integration vector contains a DNA molecule which comprises the promoter derived from the gene (SEQ ID NO:26) which codes for *Bacillus pumilus* PRL B12 xylanase, a presequence and the nucleotide sequence (SEQ ID NO:1) which codes for *Bacillus* sp. 720/1 xylanase or a modified sequence derived from this sequence. In a usual variant, the expression vector contains a DNA molecule which comprises a promoter, the presequence (SEQ ID NO:27) which codes for the signal peptide of *Bacillus pumilus* PRL B12 xylanase and the nucleotide sequence (SEQ ID NO:1) which codes for *Bacillus* sp. 720/1 xylanase or a modified sequence derived from this sequence. Preferably, the expression vector or the chromosome integration vector contains a DNA molecule which comprises the promoter derived from the gene (SEQ ID NO:26) which codes for *Bacillus pumilus* PRL B12 xylanase, the presequence (SEQ ID NO:27) which codes for the signal peptide of *Bacillus pumilus* PRL B12 xylanase and the nucleotide sequence (SEQ ID NO:1) which codes for *Bacillus* sp. 720/1 xylanase or a modified sequence derived from this sequence. As a special preference, this vector is the expression vector pBPXD-PRE-720X. Good results have also been obtained with the expression vector pC-BPX-PRE-720X.

The invention also relates to an expression system which can be used for the production of a polypeptide.

This expression system comprises:
  the sequence of the promoter (SEQ ID NO:26) derived from the gene which codes for *Bacillus pumilus* PRL B12 xylanase,
  a sequence coding for a signal peptide, and
  the sequence of the polypeptide of interest.

Generally, the expression system comprises the sequence of a terminator.

In a variant, this expression system comprises:
  the sequence of a promoter,
  the presequence (SEQ ID NO:27) which codes for the signal peptide of *Bacillus pumilus* PRL B12 xylanase, and
  the sequence of the polypeptide of interest.

Generally, the expression system comprises the sequence of a terminator.

Usually, this expression system comprises:
  the sequence of the promoter (SEQ ID NO:26) derived from the gene which codes for *Bacillus pumilus* PRL B12 xylanase,
  the presequence (SEQ ID NO:27) which codes for the signal peptide of *Bacillus pumilus* PRL B12 xylanase,
  the sequence of the polypeptide of interest, and
  the sequence of a terminator.

Preferably, the polypeptide of interest is an enzyme such as a hydrolase. As a special preference, the polypeptide of interest is a protease, a lipase, a xylanase, a cellulase, an amylase or a pullulanase. Good results have been obtained with the xylanase naturally produced by *Bacillus* sp. strain 720/1, that is to say when, in the expression system, the sequence of the polypeptide corresponds to the nucleotide sequence (SEQ ID NO:1) which codes for *Bacillus* sp. 720/1 xylanase.

The present invention also relates to recombinant strains into which the gene coding for a xylanase is introduced by genetic engineering techniques. The gene may be introduced by means of a replicative vector, or integrated in the host's chromosome in one or more copies by means of an integrative vector; the nucleotide sequence coding for a xylanase may be introduced by transformation, either in integrated form in the chromosomal DNA, or in self-replicating form (plasmid).

The invention also relates to strains of microorganisms which are different from the initial producer organism, into which strains the nucleotide sequence coding for a xylanase is introduced by transformation, either in integrated form in the chromosomal DNA, or in self-replicating form (plasmid); the gene coding for a xylanase may be introduced by means of a replicative vector or integrated in the host's chromosome in one or more copies by an integrative vector.

The invention relates to a transformed strain comprising the DNA molecule which contains the structural gene which codes for the mature xylanase of *Bacillus* sp. 720/1. Generally, the transformed strain is a strain of bacterium. Usually, the transformed strain is chosen from *Escherichia*, *Pseudomonas* or *Bacillus* strains. Preferably, the transformed strain is a *Bacillus* strain. As a special preference, the transformed *Bacillus* strain is a *Bacillus licheniformis* strain, a *Bacillus pumilus* strain, a *Bacillus alcalophilus* strain or a *Bacillus* sp. strain 720/1. Good results have been obtained with a *Bacillus licheniformis* strain and with a *Bacillus pumilus* strain.

The invention relates to the transformed *Bacillus* strain comprising the expression vector or the chromosomal integration vector which comprises this DNA molecule. Preferably, the transformed *Bacillus* strain is a *Bacillus licheniformis* strain. Preferably also, the transformed *Bacillus* strain is a *Bacillus* sp. strain 720/1.

The present invention also relates to the xylanase produced by a transformed strain as defined above.

The present invention also relates to a method for the production of a xylanase, comprising the culturing of an aerobic bacterium capable of producing the xylanase in a suitable nutrient medium containing carbon and nitrogen sources and inorganic salts under aerobic conditions, and the harvesting of the xylanase thereby obtained. This culture medium can be solid or liquid. Preferably, the culture medium is liquid. Preferably, the aerobic bacterium is a *Bacillus* strain or a derivative of this strain capable of producing the xylanase.

The present invention also relates to a method for the production of a xylanase, comprising the culturing of *Bacillus* sp. strain 720/1 or a derivative of this strain capable of producing the xylanase in a suitable nutrient medium containing carbon and nitrogen sources and inorganic salts under aerobic conditions, and the harvesting of the xylanase thereby obtained.

The invention also relates to a method for the preparation of a xylanase from a recombinant organism, the method comprising the isolation of a DNA fragment coding for the xylanase, the insertion of this DNA fragment into a suitable vector, the introduction of this vector into a suitable host or the introduction of this DNA fragment into the chromosome of a suitable host, the culturing of this host, the expression of the xylanase and the harvesting of the xylanase. The suitable host is generally chosen from the group consisting of *Escherichia coli*, *Bacillus* or *Aspergillus* microorganisms. Usually, the host is chosen from *Bacillus* species. Preferably, the host is chosen from microorganisms of the genus *Bacillus* (aerobic).

As a special preference, the host is chosen from the microorganisms *Bacillus subtilis*, *Bacillus licheniformis*, *Bacillus alcalophilus*, *Bacillus pumilus*, *Bacillus lentus*, *Bacillus amyloliquefaciens* or *Bacillus* sp. 720/1. Good results have been obtained when the host for the expression of the xylanase according to the present invention is a recombinant strain derived from *Bacillus licheniformis*, and preferably *Bacillus licheniformis* strain SE2 delap1 and *Bacillus licheniformis* strain SE2 delap6. *Bacillus licheniformis* strain SE2 delap1 and *Bacillus licheniformis* strain SE2 delap6 are described in European Patent Application 0,634,490, which is incorporated by reference in this application.

The invention also relates to a xylanase produced heterologously by a microorganism of the genus *Bacillus*. Usually, the microorganism of the genus *Bacillus* contains a gene coding for an alkaline protease when it is in the wild-type state. Preferably, this microorganism is a *Bacillus licheniformis* strain comprising the DNA molecule which comprises the nucleotide sequence which codes for *Bacillus* sp. 720/1 xylanase. As a special preference, the gene coding for the alkaline protease has been removed by deletion from this *Bacillus* strain. This strain is preferably *Bacillus licheniformis* strain SE2 delap1 or *Bacillus licheniformis* strain SE2 delap6.

Produced heterologously is understood to mean a production which is not performed by the natural microorganism, that is to say the microorganism which, in the wild-type state, contains the gene which codes for the xylanase.

The conditions of culture of these bacteria, such as components of the nutrient medium, culture parameters, temperature, pH, aeration and agitation, are well known to a person skilled in the art. Examples of such techniques are described, in particular, in Ullmann's Encyclopedia of Industrial Chemistry, 1987, 5th Edition, Vol. A9, pages 363-390.

The techniques of harvesting of xylanase are well known to a person skilled in the art, and are chosen according to the uses envisaged for the xylanase. Usually, centrifugation, filtration, ultrafiltration, evaporation, microfiltration, crystallization or a combination of one or other of these techniques is used, such as a centrifugation followed by an ultrafiltration. Examples of such techniques are described, in particular, by R. Scriban, Biotechnology, (Technique et Documentation Lavoisier), 1982, pp. 267-276 and in Ullmann's Encyclopedia of Industrial Chemistry, 1987, 5th Edition, Vol. A9, pages 363-390.

The xylanase can then be purified, if necessary and according to the uses envisaged. Enzyme purification techniques are well known to a person skilled in the art, such as precipitation using a salt such as ammonium sulphate, or using a solvent such as acetone or an alcohol. Examples of such techniques are described, in particular, by R. Scriban, Biotechnology, (Technique et Documentation Lavoisier), 1982, pp. 267-276.

The xylanase may also be dried by atomization or lyophilization. Examples of such techniques are described, in particular, by R. Scriban, Biotechnology, (Technique et Documentation Lavoisier), 1982, pp. 267-276 and in Ullmann's Encyclopedia of Industrial Chemistry, 1987, 5th Edition, Vol. A9, pages 363-390.

The present invention also relates to enzyme compositions comprising the xylanase according to the invention and at least one additive. These additives are known to a person skilled in the art and are chosen according to the use envisaged for the composition. They must be compatible with the xylanase and must have little or no effect on the enzyme activity of the xylanase. Usually, these additives are enzyme stabilizers, preservatives and formulation agents.

The compositions comprising the xylanase of the present invention may be used in solid or liquid form.

The xylanase is formulated according to the anticipated uses. Stabilizers or preservatives may also be added to the enzyme compositions comprising the xylanase according to the invention. For example, it is possible to stabilize the xylanase by adding propylene glycol, ethylene glycol, glycerol, starch, xylan, a sugar such as glucose and sorbitol, a salt such as sodium chloride, calcium chloride, potassium sorbate and sodium benzoate or a mixture of two or more of these products. Good results have been obtained with propylene glycol. Good results have been obtained with sorbitol.

The xylanase according to the invention has numerous outlets in various industries such as, for example, the food industries, the pharmaceutical industries or the chemical industries.

The xylanase may be used, in particular, in bakery. An example of use of a xylanase in bakery is described, in particular, in International Patent Application WO 94/04664.

The xylanase can be used, in particular, for the treatment of paper pulp. An example of the use of a xylanase for the treatment of paper pulp is described, in particular, in European Patent Application 0,634,490. The xylanase of the present invention is effective, in particular, on the pulp originating from eucalyptus wood, as illustrated in Example 13 of the present patent application.

The xylanase can be used, in particular, in animal feeds. An example of a use of a xylanase in animal feeds is described, in particular, in European Patent Application 0,507,723.

FIG. 1 (FIG. 1a and FIG. 1b) shows the nucleotide sequence (SEQ ID NO:2) coding for the mature xylanase, together with its translation into amino acids.

FIG. 2 (FIG. 2a and FIG. 2b) shows the nucleotide sequence (SEQ ID NO:11) of the gene coding for xylanase, together with its translation into amino acids.

FIG. 3 shows the restriction map of plasmid pUBR2002.

FIG. 4 shows the restriction map of plasmid pUBR-720×1.

FIG. 5 shows the restriction map of plasmid pUBR-720X11.

FIG. 6 shows the restriction map of plasmid pUBRD-720X11.

FIG. 7 shows the restriction map of plasmid pUBC2001.

FIG. 8 shows the restriction map of plasmid pC-BPX-PRE-2003

FIG. 9 shows the restriction map of plasmid pC-BPX-PRE-720X.

FIG. 10 shows the restriction map of plasmid pBPXD-PRE-720X.

FIG. 11 shows the promoter (SEQ ID NO:26) derived from the gene which codes for *Bacillus pumilus* PRL B12 xylanase.

FIG. 12 shows the presequence (SEQ ID NO:28) which codes for the signal peptide of *Bacillus pumilus* PRL B12 xylanase.

The meaning of the abbreviations and symbols used in these figures is collated in the following table.

| Symbol Abbreviation | Meaning |
|---|---|
| OriEC | origin of replication in *E. coli* |
| REP | protein needed for replication in *Bacillus* |
| Ori+ | origin of replication of the + strand in *Bacillus* |
| Ori− | origin of replication of the − strand in *Bacillus* |

-continued

| Symbol Abbreviation | Meaning |
|---|---|
| AmpR | gene conferring resistance to ampicillin |
| KmR | gene conferring resistance to kanamycin |
| BlmR | gene conferring resistance to bleomycin |
| 5'720XYL | 5' sequence located upstream of the sequence coding for *Bacillus* sp. 720/1 xylanase |
| 3'720XYL | 3' sequence located downstream of the sequence coding for *Bacillus* sp. 720/1 xylanase |
| 720XYL | sequence coding for the *Bacillus* sp. 720/1 xylanase precursor |
| 5'BPUXYL-PRE | promoter and ribosome binding site of *Bacillus pumilus* PRL B12 xylanase, followed by the presequence of *Bacillus pumilus* PRL B12 xylanase |
| 720XYL-MAT | sequence coding for the mature portion of *Bacillus* sp. 720/1 xylanase |

The present invention is illustrated by the examples which follow.

EXAMPLE 1

Isolation and Characterization of *Bacillus* sp. Strain 720/1

*Bacillus* sp. strain 720/1 was isolated from a sample of soil, obtained in Argentina, on a nutrient agar medium, and selected for its capacity to degrade a coloured xylan derivative known by the name of AZCL-xylan and sold by the company Megazyme.

This strain was cultured at 37° C. in LBS/C growth medium whose composition is as follows: wheat bran 10 g/l, Tryptone (Difco) 10 g/l, yeast extract 5 g/l, NaCl 10 g/l, $Na_2CO_3$ 5.3 g/l, $NaHCO_3$ 4.2 g/l.

The sodium carbonate and bicarbonate are sterilized separately and then added aseptically to the other components of the sterile medium. The agar medium contains, in addition, 20 g/l of agar. The strain of the present invention was identified by its biochemical features: aerobic Gram positive bacterium which takes the form of a rod; it forms an endospore. Hence it belongs to the genus *Bacillus*.

The vegetative cells of this strain in culture on LBS/C agar medium at 37° C. have a *bacillus* shape 0.8×3.0-5 µm in size. The mobility of the vegetative cells is positive.

After growth for 13 days at 37° C. on TSA agar medium, microscopic observation reveals the presence of sporangia. TSA agar medium contains 15 g/l of Tryptone (Difco), 5 g/l of soya bean peptone, 5 g/l of NaCl and 15 g/l of agar.

The strain is oligosporogenous.

The test for catalase is positive in the presence of 10% (v/v) of hydrogen peroxide. The test for oxydase is positive in the presence of 1% (w/v) of tetramethyl-1,4-phenylenediammonium dichloride.

This strain is aerobic, that is to say grows under aerobic conditions. It does not grow under anaerobic conditions, that is to say under an atmosphere of 84% (v/v) $N_2$, 8% (v/v) $CO_2$, 8% (v/v) $H_2$ at 37° C. The abbreviation % (v/v) represents a percentage expressed in terms of volume per volume.

This strain is not thermophilic. It displays normal growth after incubation in LBS/C agar medium at 20° C., 30° C., 37° C. and 45° C.; in contrast, it does not grow at 50° C. and 55° C., or at 10° C.

It displays normal growth after incubation in LBS/C agar medium in the presence of NaCl at concentrations of 2.0% (w/v) and 3.5% (w/v), and displays slight growth in the presence of 5.0% (w/v) and 7.0% (w/v) NaCl. The abbreviation % (w/v) represents a percentage expressed in terms of weight per volume.

Bacillus sp. strain 720/1 does not acifify glucose.

Bacillus sp. strain 720/1 has been identified by means of the API 50 CHB strip and the API 20 E strip following the instructions for use of the supplier (API System, France). Bacillus sp. strain 720/1 utilises glycerol, N-acetylglucosamine, arbutin, citrate, galactose, amygdalin and melibiose, and hydrolyses gelatin. These features differentiate Bacillus sp. strain 720/1 clearly from a Bacillus pumilus strain. In effect, a Bacillus pumilus strain does not display any of these features.

Bacillus sp. strain 720/1 was also identified by means of the Biolog system (USA). The data bank analysing the results of this system gives a score of 0.564 for Bacillus coagulans, 0.097 for Bacillus subtilis, 0.057 for Bacillus licheniformis and 0.00 for Bacillus pumilus. These features differentiate Bacillus sp. strain 720/1 clearly from a Bacillus coagulans strain, a Bacillus subtilis strain, from a Bacillus licheniformis strain and from a Bacillus pumilus strain.

Hence the isolated bacterium belongs to the genus Bacillus; no known species could be determined.

Bacillus sp. strain 720/1 was deposited at the collection named Belgian Coordinated Collections of Microorganisms (LMG culture collection) under the number LMG P-14798.

EXAMPLE 2

Production of Xylanase by Bacillus sp. 720/1

Bacillus sp. strain 720/1 is cultured on Petri dishes containing an LBS/C agar medium at 37° C. for 48 hours (culture A).

Then, from the culture A, culturing is carried out in an LB/C liquid medium whose composition is identical to that of LBS/C medium but without wheat bran, at 37° C. for 24 hours with orbital shaking at the rate of 250 rpm (culture B) with an amplitude of approximately 2.54 cm.

500 ml of the culture B are then transferred to a 20-1 fermenter containing 14 l of LBS/C medium. The pH is allowed to find its natural value, and the speed of agitation and the flow rate of air blown into the fermenter are such that the partial pressure of oxygen dissolved in the culture medium is not below 30% of the saturation value.

After 72 hours of culture at 37° C., the xylanase and the cellular biomass are separated by centrifugation (Beckman J21, JA10 rotor) at 8,000 rpm for 30 minutes. The xylanase produced by Bacillus sp. strain 720/1 is extracellular. From the centrifugation supernatant, the residual insoluble matter is then separated from the xylanase by microfiltration (KROS FLOII cartridge, porosity 0.2μ, company Microgon).

The microfiltration retentate is washed with 1 l of demineralized water. This washing is performed three times.

The permeate of this microfiltration is then concentrated approximately 20-fold by ultrafiltration through a Pall MICROZA SIP 1013 polysulphone cartridge having a cut-off threshold of 6 kD (company Pall).

The enzyme activity is measured on the ultrafiltration retentate (product R) and permeate (product P) obtained.

One xylanase enzyme unit (IU) is defined as the amount of enzyme which, at pH 8.0, at a temperature of 50° C. and in the presence of xylan, catalyses the liberation of glucose equivalents at the rate of 1 μmol of glucose per minute (μM [sic]/minute).

The measurement of xylanase enzyme activity is carried out according to the protocol described by Bailey, Biely and Poutanen, J. Biotechnology, 1992, 23, pages 257-270; except that the citrate-phosphate buffer mentioned by Bailey et al. was replaced by 50 mM tris(hydroxymethyl)aminoethane-HCl buffer (pH 8.0).

Sufficient polyethylene glycol (Merck polyethylene glycol reference 807490) is added to the ultrafiltration retentate (product R) to obtain a concentration of 40% (w/w). After solubilization of the polyethylene glycol, the solution obtained is incubated for 30 minutes at 25° C.

The solution containing the polyethylene glycol and the xylanase is then centrifuged for 10 minutes at 8,000 rpm (Beckman J21 centrifuge, JA10 rotor). The supernatant is removed by centrifugation. Sufficient NaCl solution (0.9% v/v) is added to the centrifugation pellet to recover the initial volume of the retentate used (product R).

Sufficient acetone is then added to this suspension containing the xylanase and NaCl to achieve a concentration of 40% (v/v). This acetone suspension is incubated for 45 minutes at 4° C.

After this incubation, this acetone suspension is centrifuged for 10 minutes at 8,000 rpm (Beckman J21, JA10 rotor).

The centrifugation supernatant is retained. To this centrifugation supernatant, acetone is added to a concentration of 80% (v/v). This acetone suspension is incubated for 45 minutes at 4° C.

After this incubation, this acetone suspension is centrifuged for 10 minutes at 8,000 rpm (Beckman J21, JA10 rotor).

The centrifugation pellet is retained. It is suspended in a sufficient volume of 0.9% (v/v) NaCl solution to be solubilized (product N).

EXAMPLE 3

Purification of the Xylanase

A fraction of the ultrafiltration retentate (product N) obtained in Example 2 is conditioned by passage through a gel permeation chromatography column (Bio-Rad Econopac 10DG column) equilibrated with 20 mM Bio-Tris(bis(2-hydroxyethyl)iminotris(hydroxymethyl)methane) buffer, pH 6.2 (buffer A). A solution designated product X is thereby obtained.

1 ml of the product X solution is then applied to an S Sepharose HP 16/10 (Pharmacia) cation exchange column previously equilibrated with the buffer A. The flow rate is 2.5 ml per minute, with an isocratic elution for 10 minutes, followed by an NaCl concentration gradient (from 10 to 50 minutes; the NaCl content rises from 0 to 0.7 M). A single peak is detected during the gradient, corresponding to the elution of the xylanase.

The fractions containing the xylanase activity (solution A) are collected.

It is verified that these fractions contain xylanase by applying 10 μl of each fraction to an agar medium comprising xylan (medium containing 0.5 g/l of AZCL-xylan, 50 mM Tris buffer (pH 8.0) and 15 g/l of agar). A halo forms around the fractions which contain xylanase.

EXAMPLE 4

Amino Acid Sequence

The amino acid sequence of the xylanase of the present invention is determined indirectly from the nucleotide sequence (SEQ ID NO:10) of the gene which codes for this xylanase, which is obtained as described in Example 14. This is carried out using the IntelliGenetics Suite Software for Molecular Biology (Release #5.4) computer program of IntelliGenetics, Inc. USA. FIG. 2 (FIG. 2a and FIG. 2b) shows the nucleotide sequence (SEQ ID NO:10) of the gene coding for the xylanase, together with its translation into amino acids (SEQ ID NO:11).

The xylanase is synthesized in the form of a precursor. The xylanase precursor contains 248 amino acids (SEQ ID NO:6). The nucleotide sequence (SEQ ID NO:4) coding for the xylanase precursor, as well as its translation into amino acids (SEQ ID NO:5), are identified.

The presequence of the xylanase synthesized in the form of a precursor is identified. It is a sequence of 27 amino acids (SEQ ID NO:9). The corresponding nucleotide sequence (SEQ ID NO:7) is identified.

The amino acid sequence of the mature xylanase is then identified. The mature xylanase contains 221 amino acids (SEQ ID NO:3).

FIG. 1 (FIG. 1a and FIG. 1b) shows the nucleotide sequence (SEQ ID NO:1) coding for the mature xylanase, together with its translation into amino acids (SEQ ID NO:2).

EXAMPLE 5

Amino Acid Distribution

The amino acid distribution of the mature xylanase, determined from the amino acid sequence (SEQ ID NO:3) of the xylanase (Example 4), is summarized in Table 1.

TABLE 1

| Symbol | Amino acid | Number | % (in molecular weight) |
|---|---|---|---|
| N | asparagine | 25 | 11.6 |
| Y | tyrosine | 13 | 8.6 |
| T | threonine | 18 | 7.4 |
| S | serine | 19 | 6.7 |
| I | isoleucine | 14 | 6.4 |
| V | valine | 14 | 5.6 |
| G | glycine | 24 | 5.5 |
| W | tryptophan | 7 | 5.3 |
| K | lysine | 10 | 5.2 |
| R | arginine | 8 | 5.1 |
| Q | glutamine | 9 | 4.7 |
| D | aspartic acid | 10 | 4.7 |
| L | leucine | 10 | 4.6 |
| E | glutamic acid | 8 | 4.2 |
| F | phenylalanine | 7 | 4.2 |
| P | proline | 7 | 2.8 |
| M | methionine | 5 | 2.7 |
| A | alanine | 8 | 2.3 |
| H | histidine | 4 | 2.2 |
| C | cysteine | 1 | 0.4 |
| B | aspartic acid/asparagine | 0 | 0.0 |
| X | unknown | 0 | 0.0 |
| Z | glutamine glutamic acid | 0 | 0.0 |

EXAMPLE 6

Estimation of the Molecular Weight

The molecular weight of the xylanase is estimated by calculation from the amino acid sequence of the mature form of the xylanase, as described in Example 4.

A molecular weight of 24698.61 daltons is deduced by calculation.

EXAMPLE 7

Molecular Weight Determination

Concentration on a Centricon 10 kD device (Amicon) is performed on the solution A containing the xylanase, as obtained in Example 3.

100 µl of the concentrated solution are applied to a Superdex 75 HR 10/30 (Pharmacia) gel permeation chromatography column. The column was previously calibrated by means of the (Pharmacia) Gel Filtration LMW calibration kit, code 17-0442-01, molecular weight markers. Elution took place at 0.25 ml/minute by means of 25 mM CAPSO (3-(cyclohexylamino)-2-hydroxy-1-propanesulphonic acid) buffer pH 9.2, with the addition of 0.2 M NaCl.

The chromatogram obtained shows a single peak corresponding to the xylanase activity. An apparent molecular weight of the protein of approximately 13.5 kD is deduced from this.

Polyacrylamide gel electrophoresis under denaturing conditions (SDS-PAGE) is also performed on the fraction originating from this single peak. The gel system used is the PhastSystem system of Pharmacia LKB Biotechnology, with gels containing a polyacrylamide gradient from 10-15% (v/v). Electrophoresis conditions are those prescribed by the supplier. Pharmacia LMW (Low Molecular Weight) molecular weight markers, reference 17-0446-01, are used as control. The markers employed are phosphorylase b (94 kD), albumin (67 kD), ovalbumin (43 kD), carbonic anhydrase (30 kD), trypsin inhibitor (20.1 kD) and alpha-lactalbumin (14.4 kD).

Staining with Coomassie blue reveals a polypeptide of molecular weight approximately 25.7 kD.

EXAMPLE 8

Estimation of the Isoelectric Point

The isoelectric point of the xylanase is estimated from the amino acid sequence of the mature form of the xylanase, as described in Example 4.

The estimated isoelectric point represents the net charge of the protein in denatured form.

An isoelectric point of 7.46 is deduced for the xylanase in denatured form.

EXAMPLE 9

Isoelectric Point Determination

A fraction of the solution A, as obtained in Example 3, is applied to a Mono P 5/20 chromatofocusing column (Pharmacia), following the supplier's recommendations, previously equilibrated with a 25 mM diethanolamine buffer, pH 9.9.

The column is eluted by means of the Polybuffer 96 ampholyte solution (Pharmacia) diluted 10-fold in demineralized water.

The pH of the fraction containing the xylanase activity is 9.5.

It is verified that this fraction contains xylanase by applying 10 μl of the fraction to an agar medium comprising xylan (medium containing 0.5 g/l of AZCL-xylan, 50 mM Tris buffer (pH 8.0) and 15 g/l of agar). A halo, which takes the form of a zone of hydrolysis of AZCL-xylan, forms around the fraction which contains the xylanase.

Isoelectric focusing is carried out on a fraction of the solution A as obtained in Example 3.

To do this, Pharmacia DryIEF gel is rehydrated with a mixture consisting of 2 ml of demineralized water, 150 μl of Biolyte 8-10 product (BioRad) and 75 μl of Pharmalyte 8-10.5 product (Pharmacia). Approximately 200 nanogrammes of proteins (fraction of the solution A) are applied to the gel. The protocol described by the supplier is followed.

It is deduced from this that the xylanase has an isoelectric point slightly above 9.6, the isoelectric point of the marker having the highest isoelectric point used.

The experimentally observed isoelectric point represents the surface charge of the protein in its native form.

EXAMPLE 10

Activity Profile as a Function of pH for the Xylanase Produced by the Natural Strain (*Bacillus* sp. 720/1)

The enzyme activity of the xylanase is measured according to the method described in Example 2 in the presence of xylan (Roth, reference 7500, birchwood xylan) at a temperature of 50° C. and at different pH values (from 5.6 to 10.35) in different buffers chosen to obtain the desired pH. The solution comprising the xylanase as obtained in Example 2 (product N) is employed.

The results are collated in Table 2. It may be noted that the margin of error is estimated at approximately 25% in this type of measurement.

In the course of this assay, maximal enzyme activity was measured for the sample placed at a pH of approximately 6.2 and at a temperature of approximately 50° C. for 15 minutes. By definition, a relative enzyme activity of 100% was hence assigned to this sample.

This example shows that the xylanase according to the invention develops considerable enzyme activity over a pH range between approximately 5.6 and approximately 10.

TABLE 2

| pH | Buffer used (50 mM) | Relative activity % |
|---|---|---|
| 5.6 | Tris-maleate | 85 |
| 6.2 | Tris-maleate | 100 |
| 6.8 | Tris-maleate | 96 |
| 7.5 | Tris-maleate/Tris* | 88 |
| 8.7 | Tris/Capso* | 92 |
| 9.5 | Capso/Caps* | 76 |
| 10 | Caps | 50 |
| 10.35 | Caps | 19 |

Tris = tris(hydroxymethyl)aminomethane
Tris-maleate = buffer composed of tris(hydroxymethyl)aminomethane (50 mM) and maleic acid (50 mM), in which the ratio between the components is chosen in accordance with the desired pH, the pH being adjusted by means of NaOH (1 M)
Capso = 3-(cyclohexylamino)-2-hydroxy-1-propanesulphonic acid
Caps = 3-(cyclohexylamino)-1-propanesulphonic acid
The symbol * means that the value obtained is the mean of the measurements performed at the same pH but obtained with the two buffers.

This example shows that the xylanase according to the invention develops high enzyme activity over a very wide pH range.

EXAMPLE 11

Effect of pH on the Activity of the Xylanase Produced by *Bacillus* sp. Strain 720/1 as an Aid to the Bleaching of Coniferous Wood Pulp Three aqueous suspensions of a pinewood pulp (obtained from the company SCA) are prepared, having a consistency of 2.5% (as weight of dry matter) and having an initial Kappa number of 17.

The pH of these suspensions is adjusted to pH 5

1st Stage: Enzyme Stage (Stage X)

The solution designated product N, as obtained in Example 2, is diluted with demineralized water to obtain an enzyme solution having an enzyme activity of 25 IU/ml (as described in Example 2).

This enzyme solution containing the xylanase is added to one suspension of pinewood pulp such that the pulp suspension is treated by means of 5 IU/g of dry pulp.

To the other two suspensions of pinewood pulp, demineralized water is added in place of the enzyme solution in identical proportions.

The three suspensions are then incubated for 2 hours at 50° C. without stirring.

2nd Stage: Chlorine Stage (Stage C)

Each pulp suspension thereby obtained is then subjected to a bleaching treatment which consists of a chlorination with chlorine water. This treatment takes place on a pulp having a consistency of 3% as weight of dry matter.

To this end, an amount of chlorine of 2.89 (=0.17×17) % (weight/weight of dry pulp) is added to the enzyme-treated pulp suspension and to one non-enzyme-treated pulp suspension. An amount of chlorine of 3.40 (0.20×17) % (weight/weight) is added to the other non-enzyme-treated pulp suspension.

The 3 suspensions are incubated for 1 hour at room temperature. The pulp is then washed with 40 volumes of demineralized water.

3rd Stage: Sodium Hydroxide Stage (Stage E)

An alkaline extraction is then performed, which consists in adding 2% (weight/weight of dry pulp) of NaOH to the three suspensions obtained above and which have a consistency of 5% as weight of dry matter.

The three suspensions are incubated for 1 hour 30 minutes at a temperature of 60° C. The pulp is then washed with 40 volumes of demineralized water and recovered in the form of a sheet having a whiteness of approximately 450 ISO (+/−3° ISO).

The Kappa number of the three sheets obtained is measured.

The Kappa number relates to the measurement of the amount of lignin present in the pulp. The Kappa number is a number which represents the volume (in milliliters) of 0.1 N potassium permanganate ($KMnO_4$) solution consumed by one gram of dry pulp under the conditions specified and following the procedures described in TAPPI (Technical Committee of the Association of the Pulp and Paper industry) standard #T236 cm-85 (1985).

The degree ISO relates to the measurement of brightness of the paper obtained from the pulp. This value is a factor of the reflectance of the paper obtained from the pulp under the conditions specified and following the procedures described in ISO (The International Organization for Standardization) standard #2469 published in standard #ISO 2470-1977 (F) supplementing standard #2470.

Four assays are carried out, which are identical except for the initial pH adjustment to pH 5. In effect, four assays are carried out with an aqueous suspension of pinewood pulp whose pH has been adjusted, respectively, to pH 6, pH 7, pH 8 and pH 9 instead of pH 5.

The results are collated in Table 3.

TABLE 3

| Amount of enzymes employed (IU/g) | 5 | 0 | 0 |
|---|---|---|---|
| Amount of chlorine employed (% by weight/weight of dry pulp) | 2.89 | 2.89 | 3.40 |

| Initial pH | Kappa number | | |
|---|---|---|---|
| 5 | 4.63 | 5.01 | 4.18 |
| 6 | 3.81 | / | 4.11 |
| 7 | 3.81 | 5.01 | 4.06 |
| 8 | 3.55 | / | 4.21 |
| 9 | 3.71 | 4.91 | 4.07 |

The symbol / means that the pulp suspension was not tested.

These results show that the xylanase according to the invention permits an approximately 15 to 20% reduction in the amount of chlorine for a pulp bleached to 450 ISO. Furthermore, these results are obtained both at an alkaline pH and at an acid pH. These good results are also obtained at a pH of approximately 9.

This example shows that the xylanase according to the invention displays activity over a wide pH range. In effect, the xylanase according to the invention is active over a pH range between approximately 5 and approximately 10. It is especially active for pH values above or equal to approximately 6. It is especially active for pH values below or equal to approximately 9.

EXAMPLE 12

Effect of Temperature on the Activity of the Xylanase Produced by *Bacillus* sp. Strain 720/1 as an Aid to the Bleaching of Coniferous Wood Pulp Example 11 is repeated with 5 suspensions of coniferous wood pulp at pH 8. The enzyme treatment stage is carried out at a pH of 8 and at different temperatures (55, 60 and 65° C.).

The results are collated in Table 4.

TABLE 4

| Amount of enzymes employed (IU/g) | 5 | 0 | 0 |
|---|---|---|---|
| Amount of chlorine employed (% by weight/weight of dry pulp) | 2.89 | 2.89 | 3.40 |

| Temperature ° C. | Kappa number | | |
|---|---|---|---|
| 55 | 3.89 | / | / |
| 60 | 3.64 | 4.77 | 4.09 |
| 65 | 3.49 | / | / |

The symbol / means that the pulp suspension was not tested.

It is observed that the pulp is bleached to approximately 45° ISO.

These results show that the Kappa number of the enzyme-treated pulp samples remains well below the number of the non-enzyme-treated sample.

This example shows that the xylanase according to the invention is active over a wide temperature range. It is active at a temperature of approximately 65° C.

This example also shows that the xylanase according to the invention is stable at a temperature of approximately 60° C.

EXAMPLE 13

Activity of the Xylanase Produced by *Bacillus* sp. Strain 720/1 as an Aid to the Bleaching of Eucalyptus Pulp in the ECF Sequence For this example, a eucalyptus pulp obtained from the company CEASA Mill (Spain) is employed. The pulp is treated according to an ECF ("Elemental Chlorine Free") sequence, that is to say the succession of stages constituting the sequence does not make use of elemental chlorine.

1st Stage: Oxygen Stage (Stage O)

The pulp is treated by a process employing oxygen as described in U.S. Pat. No. 4,462,864, such that a pulp having an initial Kappa number of 12.3 and an initial degree ISO of 33.4 is obtained.

Two aqueous suspensions are prepared from this oxygen-treated pulp having a consistency of 4% as weight of dry matter.

The pH of these suspensions is adjusted to pH 9 with HCl.

2nd Stage: Enzyme Stage (Stage X)

The solution designated product N, as obtained in Example 2, is diluted with demineralized water to obtain an enzyme solution having an enzyme activity of 25 IU/ml.

This enzyme solution containing the xylanase is added to one suspension of pinewood pulp such that the pulp suspension is treated by means of 10 IU/g of dry pulp.

To the other two suspensions of pinewood pulp, demineralized water is added in place of the enzyme solution.

The 3 suspensions are then incubated for 1 hour 30 minutes at 50° C. without stirring.

3rd Stage: Chlorine Dioxide Stage (Stage D)

Each pulp suspension thereby obtained is then subjected to a bleaching treatment which consists of a chlorination with chlorine dioxide. This treatment takes place on a pulp having a consistency of 3% as weight of dry matter.

To this end, an amount of chlorine dioxide of 0.6% (weight/weight of dry pulp) is added to the enzyme-treated pulp suspension and to one non-enzyme-treated pulp suspension. An amount of chlorine dioxide of 1% (weight/weight) is added to the other non-enzyme-treated pulp suspension.

The 3 suspensions are incubated for 30 minutes at 50° C. The pulp is then washed with 40 volumes of demineralized water.

4th Stage: Sodium Hydroxide/Hydrogen Peroxide Stage (Stage E/P)

An alkaline extraction is then performed, which consists in adding 1.8% (weight/weight of dry pulp) of NaOH and 0.5% (weight/weight of dry pulp) of hydrogen peroxide to the three suspensions obtained above, and which have a consistency of 12% as weight of dry matter.

The three suspensions are incubated for 1 hour 30 minutes at a temperature of 70° C. The pulp is then washed with 40 volumes of demineralized water.

5th Stage: Chlorine Dioxide Stage (Stage D)

Each pulp suspension thereby obtained is then subjected again to a bleaching treatment which consists of a chlorination with chlorine dioxide. This treatment takes place on a pulp having a consistency of 12%.

An amount of chlorine dioxide of 0.5% (weight/weight of dry pulp) is added to these three suspensions.

The 3 suspensions are incubated for 2 hours at 75° C. The pulp is then washed with 40 volumes of demineralized water.

6th Stage: Sodium Hydroxide/Hydrogen Peroxide Stage (Stage E/P)

An alkaline extraction is then performed, which consists in adding 0.6% (weight/weight of dry pulp) of NaOH and 0.3% (weight/weight of dry pulp) hydrogen peroxide to the three suspensions obtained above, and which have a consistency of 12% as weight of dry matter.

The three suspensions are incubated for 1 hour 30 minutes at a temperature of 70° C. The pulp is then washed with 40 volumes of demineralized water.

7th Stage: Chlorine Dioxide Stage (Stage D)

Each pulp suspension thereby obtained is then subjected to a bleaching treatment which consists of a chlorination with chlorine dioxide. This treatment takes place on a pulp having a consistency of 12%.

An amount of chlorine dioxide of 0.3% (weight/weight) is added to these three suspensions.

The 3 suspensions are incubated for 2 hours 30 minutes at 75° C. The pulp is then washed with 40 volumes of demineralized water and is recovered in the form of a sheet.

The degree ISO of the three sheets obtained is measured. The results are collated in Table 5.

TABLE 5

| | | | |
|---|---|---|---|
| Amount of enzymes employed in stage 2 in IU/g | 10 | 0 | 0 |
| Amount of chlorine dioxide employed in stage 3 in % (weight/weight of dry pulp) | 0.6 | 0.6 | 1.0 |
| °ISO | 88.5 | 85.5 | 87.9 |

This example shows that the xylanase according to the invention is effective on eucalyptus pulp. Furthermore, it does not necessitate any pH adjustment, since it has the advantage of being active at the pH of the pulp, that is to say at a pH of approximately 9. This example shows that the xylanase according to the invention is an alkaline xylanase.

This example also shows that, in comparison with what is obtained without xylanase, the use of the xylanase according to the invention brings about an increase in brightness of at least 3° ISO for a fixed amount of $ClO_2$.

This example also shows that the use of the xylanase according to the invention enables the amount of $ClO_2$ to be reduced by approximately 4 to 5 kg/tonne of pulp, representing approximately 25 to 30% of the total amount of $ClO_2$ needed.

EXAMPLE 14

Determination of the Nucleotide and Protein Sequence of *Bacillus* sp. 720/1 Xylanase 1. Extraction of Chromosomal DNA from *Bacillus* sp. Strain 720/1

From the culture B as obtained in Example 2, culturing of 200 ml of *Bacillus* sp. strain 720/1 is carried out in LB/C medium for 16 hours at 37° C. LB/C medium is identical to the LBS/C medium described in Example 1, without the addition of wheat bran.

When this culture has been prepared and is in stationary phase, it is centrifuged (Beckman J 21, JA10 rotor) at 5,000 rpm for 10 minutes. The centrifugation pellet thereby obtained is taken up in 9 ml of Tris-HCl (tris(hydroxymethyl) aminomethane acidified with 0.1 M HCl) buffer at pH 8, 0.1 M EDTA (ethylenediaminetetraacetic acid), 0.15 M NaCl containing 18 mg of lysozyme; the suspension thereby obtained is incubated for 15 minutes at 37° C.

The lysate thereby obtained is then treated with 200 µl of an RNAse solution at a concentration of 10 mg/ml for 20 minutes at 50° C. 1 ml of 10% (w/v) SDS (sodium dodecyl sulphate) solution is then added to this lysate. This lysate is then incubated for 30 minutes at 70° C.

The lysate is thereafter cooled to around 45° C., and 0.5 ml of a solution of proteinase K (sold by Boehringer Mannheim) at a concentration of 20 mg/ml (prepared immediately before use) is then added to it.

The lysate is incubated at 45° C. with stirring until a transparent solution is obtained.

Several phenol extractions are performed on this transparent solution under the conditions and following the procedures described in Molecular Cloning—a laboratory manual—Sambrook, Fritsch, Maniatis—second edition, 1989, on page E.3, until a clean interface is obtained, as described therein.

The DNA is precipitated with 20 ml of ethanol. The precipitate is recovered by centrifugation at 5,000 rpm (Beckman J21, JA10 rotor) for 5 minutes, and then suspended in 2 ml of TE buffer, pH 8.0, (10 mM Tris-HCl, 1 mM EDTA, pH 8.0). This suspension contains the chromosomal DNA.

2. Construction of the Vector pUBR2002

The vector pUBR2002 (*E. coli-Bacillus subtilis*) was obtained from plasmid pBR322 which is sold by the company Biolabs (Clontech Laboratories catalogue No. 6210-1) and the vector pUB131.

Two synthetic oligonucleotides are constructed by the technique described in Beaucage et al. (1981), Tetrahedron Letters, 22, pages 1859-1882 and using β-cyanoethyl phosphoramidites in a Biosearch Cyclone Synthesizer.

The sequences of these two oligonucleotides are as follows:

```
5' - CCCCCCTACGTAGCGGCCGCCCCGGCCGGTAACCTAGGAAGTCAGCGCCCTGCACC - 3'    SEQ ID NO:14
``` and

```
5' - CCCCCCTACGTAGGCCGGGCGGCCGCGGTTACCTAGGGCCTCGTGATACGCCTAT - 3'    SEQ ID NO:15
```

These two oligonucleotides are used to perform a PCR amplification on plasmid pBR322 according to the technique described in Molecular Cloning, a laboratory Manual—Sambrook et al., second edition, 1989, pages 14.18-14.19.

The PCR-amplified fragment contains the *E. coli* replicon limited on both sides by the AvrII, BstEII, NotI, SfiI, SnabI restriction sites.

The approximately 2.8-kbp (kbp=1,000 base pairs) SnabI-SnabI fragment is ligated with the vector pUB131 which has previously been subjected to digestion with SnabI. Construction of the vector pUB131 is described in Example 10 and in FIG. 7 of U.S. Pat. No. 5,352,603 (European Patent Application 0,415,296), which is incorporated by reference.

The ligation technique is described by Sambrook et al. (pages 1.68-1.69). All the ligations carried out in the examples in this application were performed according to this technique.

The ligation thereby obtained is transformed into *E. coli* MC1061 cells [Clontech Laboratories, catalogue No. C-1070-1] by electroporation (Sambrook et al., pages 1.75-1.81). The transformed cells are cultured on Petri dishes containing LB agar medium, 100 µg/ml of ampicillin and 10 µg/ml of kanamycin, at 37° C. for approximately 18 hours.

The plasmids are extracted from the colonies isolated by the alkaline lysis method (Sambrook et al., pages 1.25-1.28) and are subjected to a restriction analysis, the analysis described in Molecular Cloning, a laboratory Manual—Maniatis et al., 1982, Cold Spring Harbor Laboratory, pages 374-379.

A strain is obtained from which the vector which is designated pUBR2002 (FIG. 3) is extracted.

3. Construction of a *Bacillus* sp. 720/1 Gene Library

From the suspension containing it, the chromosomal DNA is partially cleaved with the restriction enzyme Sau3AI. The restriction conditions are those described by Sambrook et al. (pages 5.28-5.32), except that these restriction conditions are increased by a factor of 10 in order to obtain a sufficient amount of DNA for the following purification steps.

The ratio of the amount of DNA employed to the amount of enzyme is adjusted in order to obtain a maximum of fragments between 4 and 7 kbp (kbp: $10^3$ base pairs) in size.

The set of fragments thereby obtained is then subjected to agarose (0.8% w/v) gel electrophoresis as described by Sambrook et al., pages 6.01-6.19, and the fragments between 4 and 7 kbp in size are isolated and purified by the method of filtration followed by centrifugation described in Zhu et al., Bio/Technology 3, 1985, pages 1014-1016.

The DNA fragments thus purified are then ligated (according to the method described by Sambrook et al., (pages 1.68-1.69) with plasmid pUBR2002 (*E. coli-Bacillus subtilis*) previously cut at the BamHI site and dephosphorylated as described by Sambrook et al., (pages 1.60-1.61).

The ligation thereby obtained is used to transform *E. coli* MC1061 cells by electroporation (Sambrook et al., pages 1.75-1.81).

4. Screening of the Gene Library

The transformed *E. coli* cells are cultured on Petri dishes containing LB agar medium, 0.8 g/l of AZCL-xylan and 100 µg/ml of ampicillin, for approximately 24 hours at 37° C. A colony displaying a zone of hydrolysis is isolated.

The plasmid present in this colony is extracted and isolated by the alkaline lysis technique described in Sambrook et al., pages 1.25-1.28.

A restriction analysis (Sambrook et al., page 1.85) is performed. This analysis shows that the DNA fragment obtained, which contains the xylanase gene, is approximately 3.5 kbp (kbp=1,000 base pairs) in size. It is carried by the vector pUBR2002 which has been ligated.

The plasmid pUBR-720×1 (FIG. 4) is thereby obtained.

5. Cloning of a Chromosomal Fragment Containing the Xylanase Gene

Plasmid pUBR-720×1 is digested with restriction enzymes at the SwaI and SpeI sites. The xylanase gene is thereby obtained on an approximately 1.5-kbp SwaI-SpeI DNA fragment.

This SwaI-SpeI DNA fragment is subjected to a treatment with the Klenow fragment of DNA polymerase (Sambrook et al., pages F.2-F.3).

The DNA preparation thereby obtained is ligated with the vector pUBR2002 which has previously been digested with EcoRV and dephosphorylated.

The ligation is then transformed into *E. coli* MC1061 cells by electroporation.

The transformed strains are selected on Petri dishes containing LB (Luria-Bertani) agar medium, 0.8 g/l of AZCL-xylan (Megazyme) and 100 µg/ml of ampicillin, after growth at 37° C. for approximately 24 hours.

Colonies displaying a zone of hydrolysis are isolated. The plasmids are extracted from the colonies isolated by the alkaline lysis technique (Sambrook et al., pages 1.25-1.28), and are subjected to a restriction analysis (Maniatis et al., 1982, pages 374-379). This restriction analysis shows that the plasmid isolated, pUBR-720X11 (FIG. 5), contains the xylanase gene on an approximately 1.5 kbp fragment of the *Bacillus* sp. 720/1 chromosomal DNA.

Plasmid pUBR-720X11 is then used to transform *E. coli* JM109 cells (Clontech Laboratories catalogue No. C1005-1) by the CaCl$_2$ technique (Sambrook et. al., pages 1.82-1.84).

The transformed *E. coli* cells are cultured on Petri dishes containing LB agar medium, 0.8 g/l AZCL-xylan and 100 µg/ml of ampicillin. After growth at 37° C. for approximately 24 hours, a zone of hydrolysis is observed around the colonies. This shows that the transformed *E. coli* cells do indeed express the xylanase.

The technique enabling the DNA fragments to be dephosphorylated or the vectors to be linearized is described by Sambrook et al., (pages 1.60-1.61).

A colony displaying a zone of hydrolysis is isolated. The plasmid present in this colony is extracted and isolated by the alkaline lysis technique.

The sequence of the xylanase is established using the method described in Sambrook et al. pages 13.15 and 13.17 (FIG. 13.3B), using plasmid pUBR-720X11 as template.

To initiate the sequence determination, synthetic oligonucleotides are prepared for hybridization with plasmid pUBR2002. The sequences of these synthetic ologonucleotides are as follows:

```
                                            SEQ ID NO:16
5' - ACGAGGAAAGATGCTGTTCTTGTAAATGAGT - 3' and

5' - TACCTTGTCTACAAACCCC - 3'          SEQ ID NO:17
```

The remainder of the sequence is determined by the use of other synthetic oligonucleotides chosen on the basis of the newly determined portions of the sequence.

The nucleotide sequence of the complete gene which codes for xylanase (SEQ ID NO:10) is thereby obtained (FIG. 2). The xylanase gene is obtained as an approximately 1.5-kbp fragment.

EXAMPLE 15

Construction of the Expression Vector pUBRD-720X11

The expression vector pUBRD-720X11 (FIG. 6) is a plasmid derived from plasmid pUBR-720X11 from which the *E. coli* replicon has been removed.

The construction of plasmid pUBRD-720X11 from plasmid pUBR-720X11, as obtained in Example 14, is described below.

Plasmid pUBR-720X11 is digested with the restriction enzyme at the SnaBI sites for the purpose of removing the origin of replication of *E. coli*, according to the technique described in Example 14. An approximately 5-kbp fragment is thereby obtained; it is ligated with itself according to the technique described in Example 14, to obtain plasmid pUBRD-720X11.

The ligation thereby obtained is used to transform competent *Bacillus subtilis* SE3 cells according to the technique described in DNA Cloning, vol. 11, ed. Glover, D. M., IRL Press Oxford, 1985, pages 9-11.

*Bacillus subtilis* strain SE3 was deposited on 21 Jun. 1993 at the collection named Belgian Coordinated Collections of Microorganisms (LMG culture collection, Ghent, Belgium) in accordance with the Budapest Treaty under the number LMG P-14035.

The transformed cells are cultured on Petri dishes containing LB (Luria-Bertani) agar medium, 0.8 g/l of AZCL-xylan and 25 µg/ml of kanamycin, at 37° C. for approximately 18 hours. After growth, colonies displaying a zone of hydrolysis are isolated.

The isolated colonies are subjected to a plasmid analysis by enzyme restriction for the purpose of verifying that the construction of the plasmid is correct, according to the technique described in Example 14.

A strain is obtained from which the vector which is designated pUBRD-720X11 may be isolated.

EXAMPLE 16

Transformation of *Bacillus licheniformis* Strain SE2 delap6 with the Expression Vector pUBRD-720X11

Plasmid pUBRD-720X11 described in Example 15 is extracted from its host, isolated and purified (Sambrook et al., 1989, p. 1.25-1.28).

A culture of *Bacillus licheniformis* strain SE2 delap6 is prepared. *Bacillus licheniformis* strain SE2 delap6 and the culturing thereof are described in Examples 27 and 28 of European Patent Application 0,634,490, which is incorporated by reference.

*Bacillus licheniformis* strain SE2 delap6 was prepared from *Bacillus licheniformis* strain SE2, which was deposited on 21 Jun. 1993 at the collection named Belgian Coordinated Collections of Microorganisms (LMG culture collection, Ghent, Belgium) in accordance with the Budapest Treaty under the number LMG P-14034.

*Bacillus licheniformis* strain SE2 delap6 is then transformed with plasmid pUBRD-720X11 according to the protoplast technique (Maniatis et al., p. 150-151).

The transformed strain [*Bacillus licheniformis* SE2 delap6 (pUBRD-720X11)] is selected on Petri dishes containing LB agar medium, 0.8 g/l of AZCL-xylan and 25 µg/ml of kanamycin. It is then isolated and purified by screening, that is to say by being applied and streaked to obtain single colonies at the surface of LB (Luria-Bertani) agar medium which is described in Molecular Cloning-Laboratory Manual (Sambrook et al.), 1989, p. A.4.

EXAMPLE 17

Production of Xylanase by *B. licheniformis* SE2 delap6 (pUBRD-720X11)

*B. licheniformis* strain SE2 delap6 transformed by plasmid pUBRD-720X11, as obtained in Example 16, is cultured for 17 hours at 37° C. in an LB culture medium supplemented with 0.5% (w/v) of glucose and 20 µg/ml of kanamycin.

This culture is transferred (5% v/v) to 50 ml of M2 medium supplemented with 20 µg/ml of kanamycin.

M2 medium contains 30 g of soya flour, 75 g of soluble starch, 2 g of sodium sulphate, 5 mg of magnesium chloride, 3 g of $NaH_2PO_4$, 0.2 g of $CaCl_2.H_2O$ and 1,000 ml of water. The pH of this M2 medium is adjusted to 5.8 with 10 N NaOH before it is sterilized.

The culture is incubated with orbital shaking at the rate of 250 rpm with an amplitude of approximately 2.54 cm for 80 hours at 37° C. After 80 hours, the biomass is removed by centrifugation (Beckman J21, JA10 rotor) at 5,000 rpm for 10 minutes. The centrifugation supernatant is retained. The enzyme activity is measured on this supernatant according to the technique described in Example 2, and the presence of an xylanase activity is noted.

EXAMPLE 18

Construction of the Vector pUBC2001

The vector pUBC2001 (*E. coli-Bacillus*) (FIG. 7) is a plasmid derived from the plasmid pUBC131 containing, as sole difference, the presence of two additional restriction sites: BstEII and PacI. Construction of the vector UBC131 is described in Example 11 and in FIG. 8 of U.S. Pat. No. 5,352,603 (European Patent Application 0,415,296), which is incorporated by reference.

The construction of this plasmid is described below.

Four synthetic oligonucleotides are constructed according to the technique described in Example 14.

The sequences of these four oligonucleotides are as follows:

```
5' - CGGTCGCCGCATACACTA - 3'                                               SEQ ID NO:18

5' - CCCCCCCCCGGTAACCTGCATTAATGAATCGGCCAA - 3'                             SEQ ID NO:19

5' - CCCCCCCCCGGTTACCGTATTTATTAACTTCTCCTAGTA - 3'                          SEQ ID NO:20

5' - CCCCCCTCTAGATTAATTAACCAAGCTTGGGATCCGTCGACCTGCAGATC - 3'               SEQ ID NO:21
```

The two oligonucleotides having the sequences SEQ ID NO: 18 and 19 are used to perform a PCR amplification on the vector pUBC131 according to the PCR technique described in Example 14. The PCR-amplified fragment, containing a portion of the ampicillin resistant gene and the functions needed for replication in *E. coli*, is subjected to a restriction with ScaI and BstEII, generating an approximately 1.5-1.6-kbp fragment.

A second PCR amplification is carried out on the vector pUBC131, using the oligonucleotides having the sequences SEQ ID NO: 20 and 21 and according to the technique described in Example 14. The PCR-amplified fragment contains a portion of the vector pUBC131. This fragment is subjected to a restriction with BstEII and EcoRI, generating an approximately 1.4-1.5-kbp fragment.

The two fragments thereby obtained are ligated together, according to the technique described in Example 14, with the vector pUBC131 which has previously been subjected to a double digestion with EcoRI and ScaI, according to the technique described in Example 14.

The ligation thereby obtained is used to transform *E. coli* MC1061 cells by electroporation according to the technique described in Example 14. The transformed cells are cultured on Petri dishes containing LB agar medium, 100 μg/ml of ampicillin and 10 μg/ml of kanamycin, at 37° C. for approximately 18 hours.

After growth, the isolated colonies are subjected to a plasmid analysis by enzyme restriction according to the technique described in Example 14.

A strain is obtained from which the vector which is designated pUBC2001 may be extracted.

EXAMPLE 19

Construction of the Expression Vector
pC-BPX-PRE-2003

The expression vector pC-BPX-PRE-2003 (*E. coli-Bacillus*) (FIG. 8) is an expression vector derived from plasmid pUBC2001. It contains the promoter derived from the gene which codes for *Bacillus pumilus* PRL B12 xylanase and the presequence which codes for the signal peptide of *Bacillus pumilus* PRL B12 xylanase. The method for preparing and obtaining the promoter derived from the gene which codes for *Bacillus pumilus* PRL B12 xylanase and the presequence which codes for the signal peptide of *Bacillus pumilus* PRL B12 xylanase is described in Example 17 and in FIG. 1 of European Patent Application 0,634,490, which is incorporated in this application by reference.

The sequence of the promoter derived from the gene which codes for *Bacillus pumilus* PRL B12 xylanase is described in the present application under the number SEQ ID NO: 26. The sequence of the presequence which codes for the signal peptide of *Bacillus pumilus* PRL B12 xylanase is described in the present application under the number SEQ ID NO: 27.

The construction of plasmid pC-BPX-PRE-2003 is described below.

Two synthetic oligonucleotides are constructed according to the technique described in Example 14.

The sequences of these two oligonucleotides are as follows:

```
                                        SEQ ID NO:22
5' - CCCCCCTGAAATCAGCTGGACTAAAAGGGATGCAATTTC - 3'
```

```
                                        SEQ ID NO:23
5' - CCCCCCGTCGACCGCATGCGCCGGCACAGC - 3'
```

These two oligonucleotides are used to perform a PCR amplification on the plasmid pUB-BPX12 according to the technique described in Example 14. Construction of the plasmid pUB-BPX12 is described in Example 17 and in FIG. 4 of European Patent Application 0,634,490, which is incorporated by reference.

The use of the oligonucleotide having the sequence SEQ ID NO: 22 makes it possible, by changing one nucleotide, to remove, upstream of the *B. pumilus* PRL B12 xylanase promoter, the SphI restriction site, located at approximately 5.5 kbp, normally present in pUBC2001. The change of nucleotide is represented by the nucleotide underlined in the sequence SEQ ID NO: 22 above, and relates to the replacement of C by G for the SphI site (SphI=GCATGC).

The sequence SEQ ID NO: 23 enables a new SphI site to be created at the end of the presequence which codes for the signal peptide of *B. pumilus* PRL B12 xylanase, by changing only one nucleotide of the Ala codon [25], that is to say by changing GCG to GCT.

The PCR amplified fragment, containing the promoter derived from the gene which codes for *B. pumilus* PRL B12 xylanase and the presequence which codes for the signal peptide of *B. pumilus* PRL B12 xylanase, is subjected to a restriction with PvuII and SphI, generating an approximately 0.7-kbp fragment, according to the technique described in Example 14.

The approximately 0.7-kbp PvuII-SphI fragment is ligated with the vector pUBC2001 which has previously been subjected to a double digestion with PvuII and SphI, according to the techniques described in Example 14.

The ligation thereby obtained is used to transform *E. coli* MC1061 cells by electroporation according to the technique described in Example 14. The transformed cells are cultured on Petri dishes containing LB agar medium, 100 μg/ml of ampicillin, at 37° C. for approximately 18 hours.

After growth, the isolated colonies are subjected to a plasmid analysis by enzyme restriction according to the technique described in Example 14.

A strain is obtained from which the vector which is designated pC-BPX-PRE-2003 may be extracted.

EXAMPLE 20

Construction of the Expression Vector
pC-BPX-PRE-720X

The expression vector pC-BPX-PRE-720X (*E. coli-Bacillus*) (FIG. 9) is an expression vector containing the promoter derived from the gene which codes for *B. pumilus* PRL B12 xylanase and the presequence which codes for the signal peptide of *B. pumilus* PRL B12 xylanase and the sequence of the gene which codes for the mature portion of *Bacillus* sp. 720/1 xylanase.

The expression vector pC-BPX-PRE-720X contains the sequence SEQ ID NO: 1, the nucleotide sequence of the gene which codes for the mature portion of *Bacillus* sp. 720/1 xylanase.

The construction of plasmid pC-BPX-PRE-720X is described below.

Two synthetic oligonucleotides are constructed according to the technique described in Example 14.

The sequences of these two oligonucleotides are as follows:

```
                                        SEQ ID NO:24
5' - CCCCCCGCATGCGCAAATCGTCACCGACAATTCCATTGG - 3'
```

```
5' - TACCTTGTCTACAAACCCC - 3'        SEQ ID NO:25
```

These two oligonucleotides are used to perform a PCR amplification on plasmid pUBR-720X11, as obtained in Example 14, and according to the technique described in Example 14.

The PCR amplified fragment containing the sequence of gene which codes for the mature portion of *Bacillus* sp. 720/1 xylanase is subjected to a restriction with SphI and SacI, generating an approximately 0.8-kbp fragment, according to the technique described in Example 14.

The SphI-SacI fragment is ligated with the vector pC-BPX-PRE-2003 which has previously been subjected to a double digestion with SphI and SacI, according to techniques described in Example 14. Ligation at the SphI restriction site enables a translational fusion of the signal sequence of the gene which codes for *B. pumilus* PRL B12 xylanase with the sequence of the gene which codes for the mature portion of *Bacillus* sp. 720/1 xylanase to be created.

The ligation thereby obtained is used to transform *E. coli* MC1061 cells by electroporation according to the technique described in Example 14. The transformed cells are cultured on Petri dishes containing LB agar medium, 0.8 g/l of AZCL-xylan and 100 μg/ml of ampicillin, at 37° C. for approximately 18 hours. Colonies displaying a zone of hydrolysis are isolated.

After growth, the isolated colonies are subjected to a plasmid analysis by enzyme restriction according to the technique described in Example 14.

A strain is obtained from which the vector which is designated pC-BPX-PRE-720X may be extracted.

EXAMPLE 21

Construction of the Vector pBPXD-PRE-720X

The vector pBPXD-PRE-720X (*Bacillus*) (FIG. 10) is an expression vector derived from plasmid pUB131. It contains the promoter derived from the gene which codes for *B. pumilus* PRL B12 xylanase and the presequence which codes for the signal peptide of *B. pumilus* PRL B12 xylanase and the sequence of the gene which codes for the mature portion of *Bacillus* sp. 720/1 xylanase.

The construction of plasmid pBPXD-PRE-720X is described below.

Plasmid pC-BPX-PRE-720X obtained in Example 20 is subjected to a restriction with PvuII and EcoRI, generating an approximately 1.5-kbp fragment, according to the technique described in Example 14.

The approximately 1.5-kbp fragment is ligated with the vector pUB131 which has previously been subjected to a double digestion with PvuII and EcoRI, according to techniques described in Example 14.

The ligation thereby obtained is used to transform *B. subtilis* SE3 cells according to the electroporation technique described in Example 14. The transformed cells are cultured on Petri dishes containing LB agar medium, 0.8 g/l of AZCL-xylan and 25 μg/ml of kanamycin, at 37° C. for approximately 18 hours. Colonies displaying a broad zone of hydrolysis are isolated.

After growth, the isolated colonies are subjected to a plasmid analysis by enzyme restriction according to the technique described in Example 14.

A strain is thereby obtained from which the vector which is designated pBPXD-PRE-720X may be extracted.

EXAMPLE 22

Transformation of *Bacillus licheniformis* SE2 delap6 with the Expression Vector pBPXD-PRE-720X Plasmid pBPXD-PRE-720X (FIG. 10) described in Example 21 is extracted from its host, isolated and purified.

A culture of *B. licheniformis* strain SE2 delap6 is prepared according to the technique described in Example 16. This strain is then transformed with this plasmid according to the protoplast technique described in Example 16.

The transformed strain [*B. licheniformis* SE2 delap6 (pBPXD-PRE-720X)] is selected from Petri dishes containing LB agar medium, 0.8 g/l of AZCL-xylan and 25 μg/ml of kanamycin. The strain is isolated and purified by screening according to the technique described in Example 16.

EXAMPLE 23

Production of Xylanase by *B. licheniformis* SE2 delap6 (pBPXD-PRE-720X)

An assay is performed which is identical to the one described in Example 17, but with *B. licheniformis* strain SE2 delap6 transformed by plasmid pBPXD-PRE-720× as obtained in Example 22.

The enzyme activity is measured according to the technique described in Example 2 on the supernatant obtained, and the presence of a xylanase activity is noted.

EXAMPLE 24

Preparation and Isolation of the Xylanase Produced by *B. licheniformis* Strain SE2 delap6 (pBPXD-PRE-720X)

The xylanase produced by *B. licheniformis* strain SE2 delap6 transformed by plasmid pBPXD-PRE-720X, as obtained in Example 22, is isolated and purified. This strain is cultured according to the protocol described in Example 23.

The xylanase obtained is isolated and purified according to the protocol described in Example 3 of European Patent Application 0,634,490, which is incorporated in this application by reference.

EXAMPLE 25

Amino Acid Sequence of the Xylanase Produced by *B. licheniformis* strain SE2 delap6 (pBPXD-PRE-720X)

The sequence of the first 50 amino acids of the xylanase produced by *B. licheniformis* strain SE2 delap6 (pBPXD-PRE-720X) is determined using a sequencing apparatus (HP G1000A, Hewlett-Packard) and according to the instruction leaflet of this apparatus.

The xylanase isolated and purified as described in Example 24 is used.

It is verified that the sequence obtained is identical to the one described in Example 4 for the xylanase produced by *Bacillus* sp. strain 720/1.

EXAMPLE 26

Determination of the Molecular Weight of the Xylanase Produced by *B. licheniformis* strain SE2 delap6 (pBPXD-PRE-720X)

The molecular weight of the xylanase produced by *B. licheniformis* strain SE2 delap6 (pBPXD-PRE-720X) is determined according to the protocol described in Example 7 and employing the xylanase isolated and purified as described in Example 24.

Staining with Coomassie blue reveals a polypeptide of molecular weight between 25 and 26 kD, which is identical to that of the xylanase produced by *Bacillus* sp. strain 720/1.

The invention claimed is:

1. An isolated DNA molecule comprising the nucleotide sequence of SEQ ID NO:4 which codes for a *Bacillus* sp. 720/1 xylanase.

2. The isolated DNA molecule according to claim 1, wherein said DNA molecule comprises a promoter comprising SEQ ID NO: 26 and a presequence comprising SEQ ID NO: 27.

3. An expression vector or chromosomal integration vector containing the DNA molecule according to claim 1 or 2.

4. A transformed *Bacillus* strain comprising the DNA molecule according to claim 1 or 2.

5. The transformed strain according to claim 4, wherein said strain is a *Bacillus licheniformis* or *Bacillus pumilus* strain.

* * * * *